(12) United States Patent
Struble et al.

(10) Patent No.: US 7,164,948 B2
(45) Date of Patent: Jan. 16, 2007

(54) CARDIAC OUTPUT MEASUREMENT USING DUAL OXYGEN SENSORS IN RIGHT AND LEFT VENTRICLES

(75) Inventors: Chester Struble, Eijsden (NL); Lambert Muhlenberg, Landgraaf (NL); Pierre-endro Grandjean, Warsaga (BE)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 10/126,710

(22) Filed: Apr. 22, 2002

(65) Prior Publication Data
US 2003/0199956 A1    Oct. 23, 2003

(51) Int. Cl.
*A61N 1/362*    (2006.01)
(52) U.S. Cl. .................................................. 607/22
(58) Field of Classification Search .................. 607/4, 607/9, 17, 18, 22–24
See application file for complete search history.

(56) References Cited

U.S. PATENT DOCUMENTS

| | | | |
|---|---|---|---|
| 3,857,399 A | 12/1974 | Zacouto | |
| 4,303,075 A | 12/1981 | Heilman et al. | |
| 4,316,472 A | 2/1982 | Mirowski et al. | |
| 4,375,817 A | 3/1983 | Engle et al. | |
| 4,379,459 A | 4/1983 | Stein | |
| 4,384,585 A | 5/1983 | Zipes | |
| 4,476,868 A | 10/1984 | Thompson | |
| 4,556,063 A | 12/1985 | Thompson et al. | |
| 4,577,633 A | 3/1986 | Berkovits et al. | |
| 4,587,970 A | 5/1986 | Holley et al. | |
| 4,726,380 A | 2/1988 | Vollmann | |
| 4,727,877 A | 3/1988 | Kallok | |
| 4,730,619 A | 3/1988 | Koning et al. | |
| 4,800,883 A | 1/1989 | Winstrom | |
| 4,802,481 A | 2/1989 | Schroeppel | |
| 4,821,723 A | 4/1989 | Baker et al. | |
| 4,880,005 A | 11/1989 | Pless et al. | |
| 4,928,688 A | 5/1990 | Mower | |

(Continued)

OTHER PUBLICATIONS

Will this function (reduction to practice, best mode)? Development of Rate Adaptive pace-Maker Based on the Maximum rate-of-Rise of Right Ventricular Pressure (RV $dp/dt_{max}$), Bennet et al., PACE, vol. 15, Feb. 92, pp. 219, 234.

(Continued)

*Primary Examiner*—Scott M. Getzow
(74) *Attorney, Agent, or Firm*—Paul H. McDowall; Girma Wolde-Michael

(57) ABSTRACT

A pacemaker provides multi-chamber pacing with a pacing interval that can be programmed and adapted in response to cardiac output measurements for a given patient. In a typical embodiment, the pacemaker may provide pacing stimuli to both ventricles of a heart. In addition, the invention may include a measurement device that incorporates first and second blood oxygen saturation sensors for deployment in the left and right ventricle. The oxygen saturation sensors provide a differential measurement that can be used to calculate cardiac output in accordance with the Fick method. The oxygen saturation sensors may be carried by a common trans-septal lead that positions one of the sensors proximate the right ventricle and the other sensor proximate the left ventricle. Alternatively, the oxygen saturation sensors may be deployed via separate leads. Whether single or dual leads are used to carry the oxygen saturation sensors, a respective lead may optionally carry electrodes for sensing, pacing, or both.

32 Claims, 13 Drawing Sheets

U.S. PATENT DOCUMENTS

| | | |
|---|---|---|
| 4,949,719 A | 8/1990 | Pless et al. |
| 4,953,551 A | 9/1990 | Mehra et al. |
| 5,099,838 A | 3/1992 | Bardy |
| 5,119,813 A | 6/1992 | Cohen |
| 5,131,388 A | 7/1992 | Pless |
| 5,136,001 A | 8/1992 | Kappler et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,243,976 A | 9/1993 | Ferek-Petric et al. |
| 5,269,298 A | 12/1993 | Adams et al. |
| 5,271,408 A | 12/1993 | Breyer et al. |
| 5,312,453 A | 5/1994 | Shelton et al. |
| 5,314,430 A | 5/1994 | Bardy |
| 5,318,595 A | 6/1994 | Ferek-Petric et al. |
| 5,330,507 A | 7/1994 | Schwartz |
| 5,331,966 A | 7/1994 | Bennet et al. |
| 5,354,316 A | 10/1994 | Keimel |
| 5,368,040 A | 11/1994 | Carney |
| 5,487,752 A | 1/1996 | Salo et al. |
| 5,514,161 A | 5/1996 | Limousin |
| 5,540,727 A | 7/1996 | Tockman et al. |
| 5,545,186 A | 8/1996 | Olson |
| 5,584,867 A | 12/1996 | Limousin et al. |
| 5,584,868 A | 12/1996 | Salo et al. |
| 5,626,623 A | 5/1997 | Kieval et al. |
| 5,728,140 A | 3/1998 | Salo et al. |
| 5,800,465 A | 9/1998 | Thompson |
| 5,891,176 A * | 4/1999 | Bornzin ...................... 607/18 |
| 6,021,350 A | 2/2000 | Mathson |
| 6,134,459 A * | 10/2000 | Roberts et al. ............. 600/333 |
| 6,466,820 B1 * | 10/2002 | Juran et al. .................... 607/9 |

OTHER PUBLICATIONS

"Automatic Tachycardia Recognition" by Arzbaecher et al. PACE May-Jun. 1984, pp. 541-547.

* cited by examiner

| PARAMETERS | CARDIAC RHYTHM GROUPS | | |
| --- | --- | --- | --- |
| | SR NOT PACED | A-(bi)V PACED | PAF VVI PACED |
| ARTERIAL SATURATION (S02) | | | |
| VENOUS SATURATION (SO2) | | | |
| CARDIAC OUTPUT (FICK) | | | |

FIG. 12

CARDIAC OUTPUT MEASUREMENT USING DUAL OXYGEN SENSORS IN RIGHT AND LEFT VENTRICLES

FIELD OF THE INVENTION

The invention relates to cardiac monitoring, and more particularly to cardiac output measurement.

BACKGROUND

Many patients that suffer from congestive heart failure (CHF) develop a wide QRS complex resulting from a delayed activation of one of the ventricles in the heart, and inter-and/or intraventricular electrical-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at significantly different times. The timing imbalance may also cause the patient to experience paradoxical septal motion, mitral regurgitation or decreased ventricular filling time.

Patients having a wide QRS complex and inter- and intra-ventricular dysynchrony may receive benefits from an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with one or more pacing leads in two or more complementary chambers of the heart. For purposes of the following discussion, the right and left atria are complementary to one another, and the right and left ventricles are complementary chambers. The right and left ventricles are complementary chambers because they receive blood from the atria and pump the blood to the heart. In a heart in a healthy patient, complementary chambers activate at approximately the same time. In a heart in a patient suffering from a condition such as CHF, complementary chambers activate at different times.

In response to a sensed or paced event, the pacemaker delivers pacing pulses or stimulations to two complementary chambers of the heart. The pacing pulses may be, but need not be, delivered simultaneously. Although the discussion that follows emphasizes bi-ventricular pacing to treat ventricular dysynchrony, cardiac resynchronization also encompasses, for example, resynchronization of atrial contractions.

Multiple-chamber pacing systems in general, and bi-ventricular and bi-atrial pacing systems in particular, are known in the art. Prior art techniques for synchronizing ventricles or atria are generally imprecise, however, and are not adaptive to changing conditions. In a typical bi-ventricular pacemaker that delivers pacing pulses to the ventricles at different times, for example, the time interval between delivery of the pacing pulses may be fixed and not automatically adjustable. Other techniques for improving hemodynamic efficiency by monitoring characteristics of heart function are known.

Examples of these techniques and/or devices may be found in the issued U.S. patents listed in Table 1 below.

TABLE 1

| U.S. Pat. No. | Inventor | Issue Date |
| --- | --- | --- |
| 5,540,727 | Tockman et al. | Jul. 30, 1996 |
| 5,891,176 | Bornzin | Apr. 6, 1999 |
| 5,119,813 | Cohen | Jun. 9, 1992 |
| 6,021,350 | Mathson | Feb. 1, 2000 |
| 4,730,619 | Koning et al. | Mar. 15, 1988 |
| 5,728,140 | Salo et al. | Mar. 17, 1998 |
| 3,857,399 | Zacouto | Dec. 31, 1974 |
| 5,584,868 | Salo et al. | Dec. 17, 1996 |
| 4,928,688 | Mower | May 29, 1990 |
| 5,626,623 | Kieval et al. | May 6, 1997 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to multiple chamber cardiac pacemakers in general, and bi-ventricular cardiac pacemakers in particular. These problems include, for example, an inability to accurately detect current cardiac output conditions and thereby adapt a pacing interval to those conditions to promote hemodynamic efficiency, as well as an inability to adapt a pacing interval to changing cardiac output conditions. Various embodiments of the present invention have the object of solving at least one of the foregoing problems.

It is an object of the invention to provide a technique for measuring cardiac output accurately and continuously, and to improve the control of a pacing interval based on the measurement. It is a further object of the invention to provide a physician with cardiac output information useful in programming a pacing interval for an implantable medical device, and to enable adaptation of the pacing interval based on continuous measurements of cardiac output during operation of the device. In addition, it is an object of the invention to provide a measurement device that can be readily deployed with little risk to a patient, and thereafter provide accurate measurements of blood oxygen saturation for use in calculation of cardiac output.

In a typical embodiment described below, the invention may be applied to bi-ventricular pacing. In this application, the interval may be called the "V1–V2 interval," which represents the time delay between delivery of pacing pulses to the ventricles. In some patients, simultaneous stimulation of the ventricles results in a lack of mechanical ventricular synchrony. The lack of synchrony may be caused by factors such as differences in placement of stimulating electrodes proximal to the ventricles or the differences in the conductive pathways of the ventricles. The lack of synchrony may cause the ventricles to begin ejection of blood at different times. For some patients, asynchronous blood ejection is inefficient and undesirable. The techniques of the invention may be useful in more accurately determining cardiac output, so that the ventricles can be brought into synchrony, resulting in improved hemodynamic performance.

Various embodiments of the invention may possess one or more features capable of fulfilling the above objects. In general, the invention may include a pacemaker that provides multi-chamber pacing with a pacing interval that can be programmed and adapted in response to cardiac output measurements for a given patient. In a typical embodiment, the pacemaker may provide pacing stimuli to both ventricles of a heart. In addition, the invention may include a measurement device that incorporates first and second sensors for deployment in the left and right ventricles, respectively, for measurement of blood oxygen saturation.

The sensors provide a differential measurement that can be used to calculate cardiac output in accordance with the Fick method. In one embodiment, the oxygen saturation sensors may be carried by a common trans-septal lead that positions one of the sensors proximate the right ventricle and the other sensor proximate the left ventricle. In another embodiment, the oxygen saturation sensors may be deployed via separate leads. Whether single or dual leads are used to carry the oxygen saturation sensors, a respective lead may optionally carry electrodes for sensing, pacing, or both. The sensors may be realized by optical sensors that emit light into blood flowing within a ventricle and receive reflected light as an indication of blood oxygen saturation.

The invention may also include a processor that computes a V1–V2 interval for bi-ventricular pacing such that pacing pulses, separated by this interval, cause the chambers to work in synchrony. In a typical application, the processor may set the interval to cause the right and left ventricles to commence blood ejection at substantially the same time in response to information including the measured cardiac output. In another application, the processor may set the interval to cause one ventricle to commence blood ejection prior to the other ventricle with a desired time offset, based on the cardiac output measured as described herein. The processor may further adjust the interval in response to changing conditions, such as a changes in heart rate, measured cardiac output, or other parameters. In addition, in some embodiments, the processor may drive a drug delivery device to deliver a drug to a patient in response to cardiac output measurements.

The invention may offer one or more advantages. Cardiac output can be measured continuously and accurately using dual oxygen saturation sensors, e.g., on a periodic basis over a series of cardiac cycles. In addition, a lead incorporating one or both of the sensors can be deployed within the ventricles to obtain a direct reading of cardiac output. When the sensors are provided in a single, trans-septal lead, deployment of the sensors can be accomplished in a single lead pass, simplifying deployment. Moreover, the transseptal deployment may place one of the oxygen saturation sensors in close proximity with the left ventricle, but without significant protrusion of the sensor, thereby avoiding excessive formation of fibrous growth and thrombosis.

By selection of an interval that separates pacing pulses delivered to the ventricles using a continuous, more accurate measurement of cardiac output, the chambers of the heart may be synchronized for near-optimal cardiac performance. When the chambers are synchronized, in accordance with measured cardiac output, the patient may experience improved cardiac performance, such as improved stroke volume and cardiac output. Moreover, the chambers of the heart may be resynchronized for near-optimal cardiac performance in response to changing cardiac output conditions measured on a continuous basis.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 12 is a chart graphically illustrating discrimination of oxygen saturation parameters for different cardiac rhythms.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
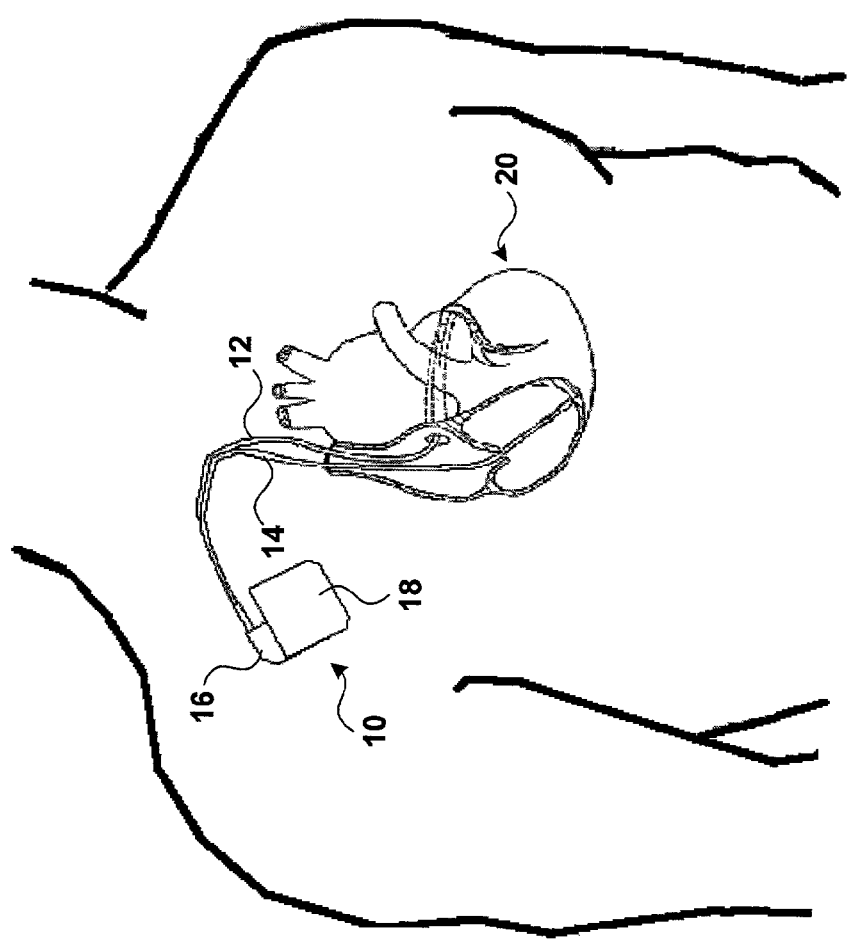
FIG. 1 is a schematic view of an exemplary implantable medical device.

FIG. 1 is a simplified schematic view of one embodiment of implantable medical device (IMD) 10 of the present invention. In accordance with the invention, IMD 10 may be configured to measure cardiac output, respond to measured cardiac output, or both. In some embodiments, IMD 10 may incorporate one or more leads carrying sensors for sensing blood oxygen saturation levels within the left and right ventricles. The blood oxygen saturation levels can be used to compute cardiac output using Fick's method. FIGS. 1–5 describe exemplary devices and contexts in which such a computation of cardiac output may be especially useful.

IMD 10 shown in FIG. 1 is a pacemaker comprising at least one pacing and/or sensing lead 12, 14 attached to connector module 16 of a hermetically sealed housing 18 and implanted near human or mammalian heart 20. Pacing and sensing leads 12, 14 sense electrical signals attendant to the depolarization and repolarization of heart 20, and further provide pacing pulses for causing depolarization of cardiac tissue in the vicinity of the distal ends thereof. Leads 12, 14 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Lead 12, 14 may also include one or more optical sensors that emit light within a chamber of the heart 20, such as the left and right ventricles, and generate a signal in response to receipt of light reflected from blood within the chamber. As will be described in more detail below, the optical sensors may generate signals indicative of blood oxygen saturation levels within the respective chambers, e.g., the left and right ventricles. The blood oxygen saturation signals may be received by IMD 10, and used in controlling therapy such as pacing or drug delivery. In some embodiments, optical sensors for sensing blood oxygen saturation levels in the left and right ventricles may be integrated in a single trans-septal lead, as will be described. Leads 12, 14, as well as a trans-septal lead, may additionally carry electrodes for sensing or delivery of pacing stimulation.

Figure 2:
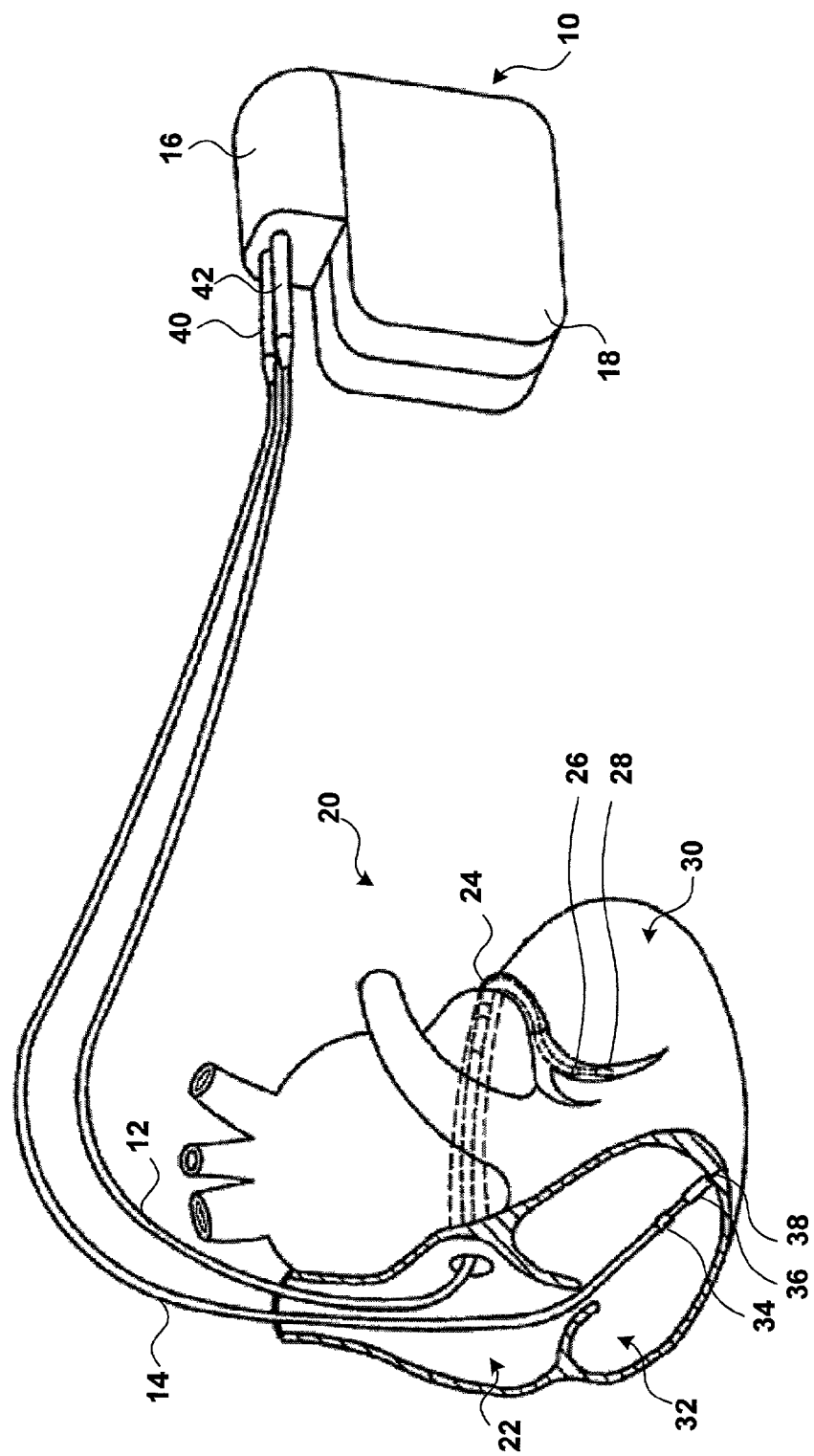
FIG. 2 shows the exemplary implantable medical device of FIG. 1 located in and near a heart.

FIG. 2 is a schematic representation of an exemplary implanted, two-channel cardiac pacemaker 10 in which the invention may be practiced. Pacemaker 10 is shown in conjunction with a human heart 20. Bipolar, endocardial left ventricular (LV) coronary sinus lead 12 is passed through a vein into the right atrium 22 of heart 20, into the coronary sinus 24 and then inferiorly in the great vein and cardiac veins extending from coronary sinus 24 to extend the distal ring pace/sense electrodes 26 and 28 alongside the LV chamber 30. The distal end of LV coronary sinus lead 12 positions ring electrodes 26 and 28 optimally with respect to the adjacent wall of left ventricle 30. Bipolar, endocardial right ventricular (RV) lead 14 is passed through the vein into right atrium 22 and into the right ventricle 32 where its distal ring and tip pace/sense electrodes 34 and 36 are fixed in place in the apex or in the interventricular septum by a distal attachment mechanism 38.

Pace/sense electrodes 26, 28, 34 and 38 sense electrical signals attendant to the depolarization and repolarization of heart 20. The electrical signals are conducted to pacemaker 10 via leads 12 and 14. Pace/sense electrodes 26, 28, 34 and 38 further deliver pacing pulses for causing depolarization of cardiac tissue in the vicinity of the distal ends thereof. The pacing pulses are generated by pacemaker 10 and are transmitted to pace/sense electrodes 26, 28, 34 and 38 via leads 12 and 14.

RV lead 14 is formed with an in-line connector 40 fitting into a bipolar bore of pacemaker connector block 16. RV lead 14 includes a pair of electrically insulated conductors that couple distal tip pace/sense electrode 36 and proximal pace/sense ring electrode 34 to pacemaker 10. LV coronary sinus lead 12 is formed with an in-line connector 42 fitting into a bipolar bore of pacemaker connector block 16. LV coronary sinus lead 12 couples distal ring pace/sense electrode 28 and proximal pace/sense ring electrode 26 to pacemaker 10.

Pacemaker 10 may deliver pacing pulses to ventricles 30, 32. Although the pacing pulses may be delivered to both ventricles 30, 32 simultaneously, in many cases there is a delay between delivery of a pacing pulse to one ventricle and a pacing pulse to the other ventricle. This delay is called the V1–V2 interval.

In general, the object of the V1–V2 interval is to promote ventricular synchrony. Due to physiological differences such as differences in conductive paths and differences in electrical-mechanical response in ventricles 30, 32, one ventricle may activate before the other when the ventricles are paced at the same time. The V1–V2 interval compensates for the physiological differences. Although the ventricles 30, 32 are paced at different times, they activate together. The hemodynamic performance of heart 20 is enhanced when ventricles 30, 32 activate synchronously.

In general, the invention presents techniques for detecting whether the ventricles are activating synchronously and adjusting the V1-V2 interval to restore synchronous activation and hemodynamic efficiency. As will be described in more detail below, the invention may also apply to synchronous activation of the atria of heart 20. Detection of hemodynamic efficiency can be performed by measuring blood oxygen saturation levels in the left and right ventricles and computing cardiac output using the measured levels, e.g., by Fick's method.

The pacing system shown in FIG. 2 is exemplary. The invention is not limited to the electrode placements shown in FIG. 2. LV pace/sense electrodes 26 and 28, for example, may be located at a site other than coronary sinus 24. RV pace/sense electrodes 34 and 36 likewise may be located at a site other than inside right ventricle 32. For example, RV pace/sense electrodes 34 and 36 may be epicardial, rather than endocardial as shown in FIG. 2. The pacing system may also include alternate or additional leads that deploy electrodes elsewhere around ventricles 30, 32, or proximal to the atria for sensing or pacing.

Furthermore, the invention is not limited to the bipolar ventricular lead systems depicted in FIG. 2. The invention may be employed with unipolar lead systems that employ a single pace/sense electrode in the depicted positions proximal to right ventricle 32 and left ventricle 30. Unipolar electrodes may cooperate with a remote electrode formed as part of the outer surface of the hermetically sealed housing 18 of pacemaker 10.

Figure 3:
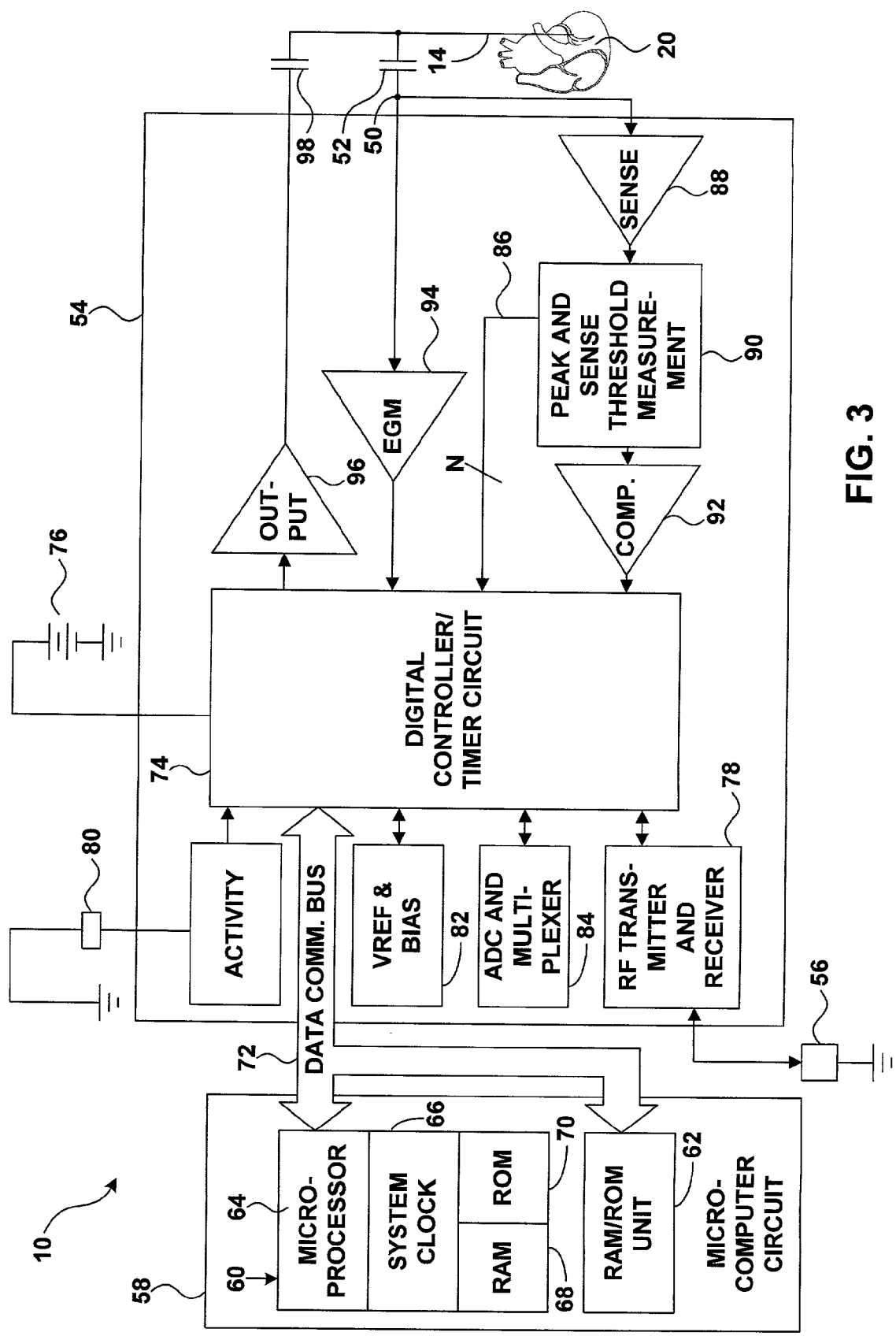
FIG. 3 is a block diagram illustrating the constituent components of the implantable medical device of FIGS. 1 and 2.

FIG. 3 shows a block diagram illustrating the constituent components of pacemaker 10 in accordance with one embodiment of the present invention. Pacemaker 10 is a pacemaker having a microprocessor-based architecture. Pacemaker 10 is shown as including activity sensor or accelerometer 44, which is preferably a piezoceramic accelerometer bonded to a hybrid circuit located inside housing 18 (shown in FIGS. 1 and 2). Activity sensor 44 typically (although not necessarily) provides a sensor output that varies as a function of a measured parameter relating to a patient's metabolic requirements. For the sake of convenience, pacemaker 10 in FIG. 3 is shown with lead 12 only connected thereto. However, it is understood that similar circuitry and connections not explicitly shown in FIG. 3 apply to lead 14 (shown in FIGS. 1 and 2).

Pacemaker 10 in FIG. 3 is most preferably programmable by means of an external programming unit (not shown in the figures). One such programmer is the commercially available Medtronic Model 9790 programmer, which is microprocessor-based and provides a series of encoded signals to pacemaker 10, typically through a programming head which transmits or telemeters radio-frequency (RF) encoded signals to pacemaker 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 12 is coupled to node 50 in pacemaker 10 through input capacitor 52. Activity sensor or accelerometer 44 is most preferably attached to a hybrid circuit located inside hermetically sealed housing 18 of pacemaker 10. The output signal provided by activity sensor 44 is coupled to input/output circuit 54. Input/output circuit 54 contains analog circuits for interfacing with heart 20, activity sensor 44, antenna 56 and circuits for the application of stimulating pulses to heart 20. The rate of heart 20 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board random access memory (RAM) 68 and read-only memory (ROM) 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of pacemaker 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of pacemaker 10 are coupled from microprocessor 64 via data bus 72 to digital controller/timer circuit 74, where digital timers and counters establish the overall escape interval of the pacemaker 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 14. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 86 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when pacemaker 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 12 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 12.

In some preferred embodiments of the present invention, pacemaker 10 may operate in various non-rate-responsive modes. In other preferred embodiments of the present invention, pacemaker 10 may operate in various rate-responsive modes. Some embodiments of the present invention are capable of operating in both non-rate-responsive and rate-responsive modes. Moreover, in various embodiments of the present invention pacemaker 10 may be programmably configured to operate so that it varies the rate at which it delivers stimulating pulses to heart 12 in response to one or more selected sensor outputs being generated. Numerous pacemaker features and functions not explicitly mentioned herein may be incorporated into pacemaker 10 while remaining within the scope of the present invention.

The present invention is not limited in scope to any particular number of sensors, and is not limited to pacemakers comprising optical sensors for blood oxygen saturation measurement only. Although the present invention is useful in multiple-chamber pacemakers, the present invention is not limited in scope to pacemakers having any particular number of sensors per lead. At least some embodiments of the present invention may be applied equally well in the contexts of dual-, triple- or quadruple-chamber pacemakers or other types of pacemakers. See, for example, U.S. Pat. No. 5,800,465 to Thompson et al., hereby incorporated by reference herein in its entirety, as are all U.S. Patents referenced therein.

Pacemaker 10 may also be a pacemaker combined with a cardioverter and/or defibrillator. Various embodiments of the present invention may be practiced in conjunction with a pacemaker-cardioverter-defibrillator such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
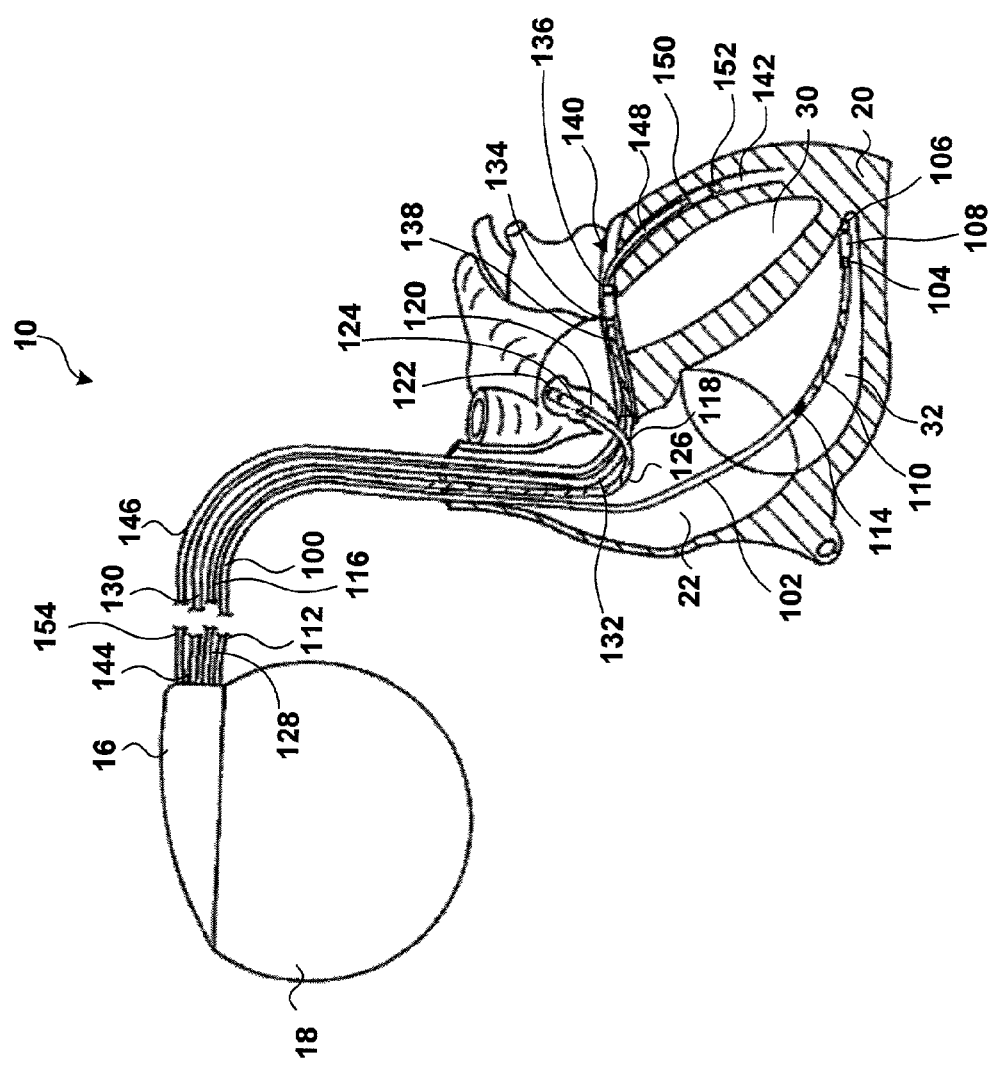
FIG. 4 shows an exemplary implantable multi-chamber medical device located in and near a heart.
Figure 5:
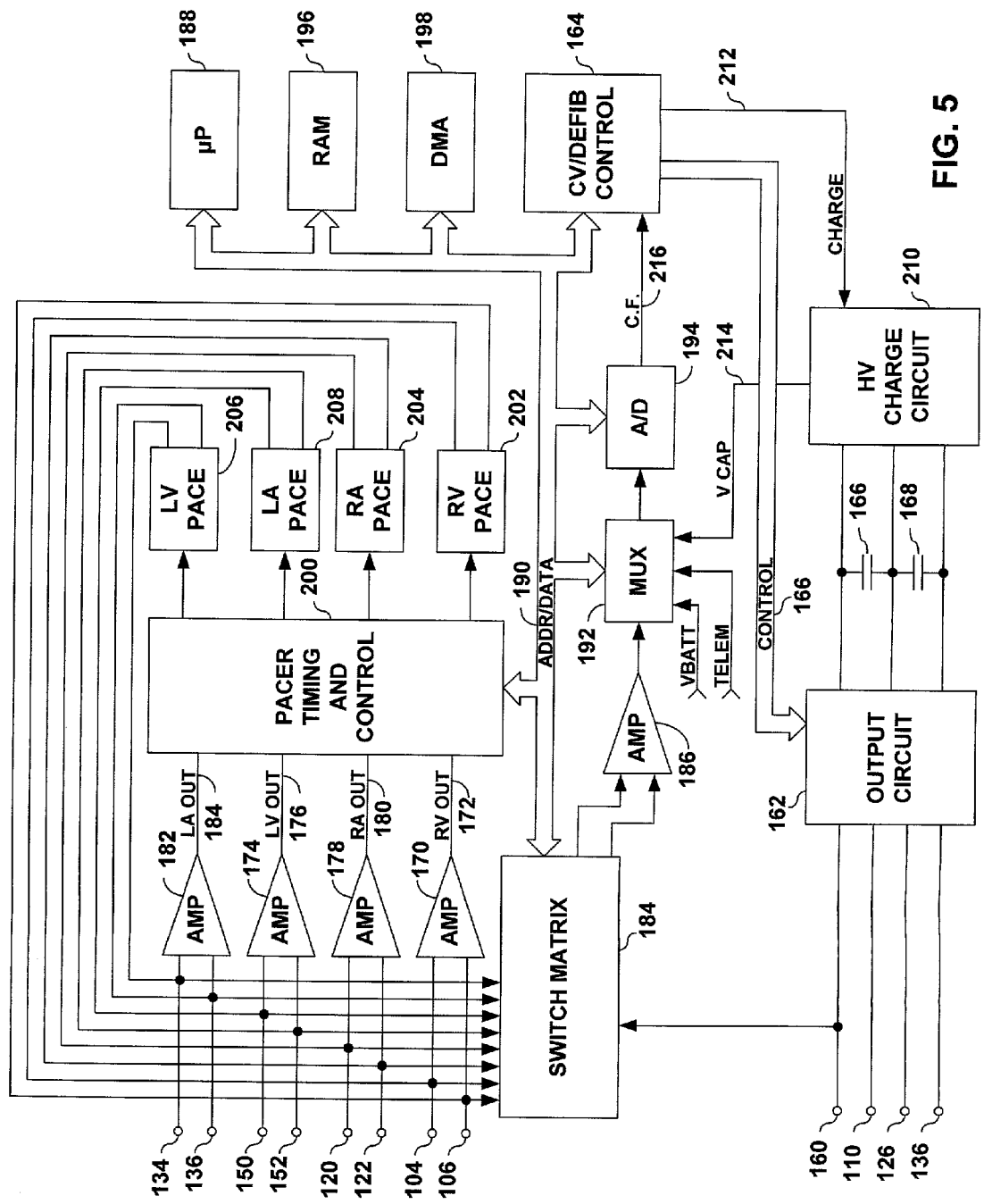
FIG. 5 is a functional schematic diagram of the embodiment of an implantable medical device shown in FIG. 4.

FIGS. 4 and 5 illustrate one embodiment of IMD 10 and a corresponding lead set of the present invention, where IMD 10 is a multi-chamber pacemaker-cardioverter-defibrillator. In FIG. 4, the right ventricular lead 100 may take the form of leads disclosed in U.S. Pat. Nos. 5,099,838 and 5,314,430 to Bardy, and includes an elongated insulative lead body 102 carrying three or more concentric coiled conductors separated from one another by tubular insulative sheaths. Located adjacent the distal end of lead 102 are ring electrode 104, extendable helix electrode 106 mounted retractably within insulative electrode head 108 and elongated coil electrode 110. Each of the electrodes is coupled to one of the coiled conductors within lead body 102. Electrodes 104 and 106 are employed for cardiac pacing and for sensing ventricular depolarizations. At the proximal end of lead 102 is a connector 112 which carries electrical connectors coupled to one of the coiled conductors. Elongated coil electrode 110, which is a defibrillation electrode 110, may be fabricated from platinum, platinum alloy or other materials known to be usable in implantable defibrillation electrodes and may be about 5 cm in length. Lead 100 may also carry a pressure sensor 114.

The atrial/SVC lead 116 shown in FIG. 4 includes elongated insulative lead body 118 carrying three concentric coiled conductors separated from one another by tubular insulative sheaths corresponding to the structure of ventricular lead 100. Located adjacent the J-shaped distal end of the lead are ring electrode 120 and extendable helix electrode 122 mounted retractably within an insulative electrode head 124. Each of the electrodes is coupled to one of the coiled conductors within lead body 118. Electrodes 122 and 120 are employed for atrial pacing and for sensing atrial depolarizations. Elongated coil electrode 126 is provided proximal to electrode 120 and coupled to the third conductor within lead body 118. Electrode 126 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is connector 128 carrying three electrical connectors, each coupled to one of the coiled conductors.

The coronary sinus lead 130 shown in FIG. 4 assumes the form of a coronary sinus lead disclosed in the above cited '838 patent issued to Bardy, and includes elongated insulative lead body 132 carrying one or more coiled conductors coupled to a ring electrodes 134 and 136 and an elongated coiled defibrillation electrode 138. Electrodes 134, 136 are employed for atrial pacing and for sensing atrial depolarizations. Electrodes 134, 136, 138 are located within the coronary sinus 140 and great vein 142 of heart 20. At the proximal end of the lead 130 is connector plug 144 carrying an electrical connector coupled to the coiled conductor. Elongated coil defibrillation electrode 132 may be about 5 cm in length.

The left ventricular lead 146 may include elongated insulative lead body 148 carrying one or more coiled conductors coupled to a ring electrodes 150 and 152. Electrodes 150, 152 are employed for ventricular pacing and for sensing ventricular depolarizations. Electrodes 150, 152 are located within the great vein 140 of heart 20. At the proximal end of the lead 146 is connector plug 154 carrying an electrical connector coupled to the coiled conductor.

IMD 10 is shown in FIG. 4 in combination with leads 100, 116, 130, 146, and lead connector assemblies 112, 128, 144, 154 inserted into connector module 16. Optionally, insulation of the outward facing portion of housing 18 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 18 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 160 in FIG. 5 includes the uninsulated portion of the housing 18 of IMD 10. Electrodes 110, 126, 136 and 160 are coupled to high voltage output circuit 162, which includes high voltage switches controlled by CV/defib control logic 164 via control bus 166. Switches disposed within circuit 162 determine which electrodes are employed and which electrodes are coupled to the positive and negative terminals of a capacitor bank (which includes capacitors 166 and 168) during delivery of defibrillation pulses.

Electrodes 104 and 106 are located on or in the right ventricle of the patient and are coupled to the R-wave amplifier 170, which preferably takes the form of an automatic gain controlled amplifier providing an adjustable sensing threshold as a function of the measured R-wave amplitude. A signal is generated on R-out line 172 whenever the signal sensed between electrodes 104 and 106 exceeds the present sensing threshold.

Similarly, electrodes 150 and 152 are located proximal to the left ventricle of the patient and are coupled to the R-wave amplifier 174, which preferably also takes the form of an automatic gain controlled amplifier providing an adjustable sensing threshold as a function of the measured R-wave amplitude. A signal is generated on R-out line 176 whenever the signal sensed between electrodes 150 and 152 exceeds the present sensing threshold.

Electrodes 120 and 122 are located on or in the right atrium of the patient and are coupled to the P-wave amplifier 178, which preferably also takes the form of an automatic gain controlled amplifier providing an adjustable sensing threshold as a function of the measured P-wave amplitude.

A signal is generated on P-out line 180 whenever the signal sensed between electrodes 120 and 122 exceeds the present sensing threshold.

Similarly, electrodes 134 and 136 are located proximal to the left atrium of the patient and are coupled to the P-wave amplifier 182, which preferably also takes the form of an automatic gain controlled amplifier providing an adjustable sensing threshold as a function of the measured P-wave amplitude. A signal is generated on P-out line 184 whenever the signal sensed between electrodes 134 and 136 exceeds the present sensing threshold. The general operation of R-wave and P-wave amplifiers 170, 174, 178, 182 may correspond to that disclosed in U.S. Pat. No. 5,117,824 to Keimel et al., hereby incorporated by reference herein in its entirety.

Switch matrix 184 is used to select which of the available electrodes are coupled to wide band (0.5–200 Hz) amplifier 186 for use in digital signal analysis. Selection of electrodes is controlled by microprocessor 188 via data/address bus 190, which selections may be varied as desired. Signals from the electrodes selected for coupling to bandpass amplifier 186 are provided to multiplexer 192, and thereafter converted to multi-bit digital signals by A/D converter 194, for storage in random access memory 196 under control of direct memory access circuit 198. Microprocessor 188 may employ digital signal analysis techniques to characterize the digitized signals stored in random access memory 196 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 200 preferably includes programmable digital counters which control the basic time intervals associated with DDD, VVI, DVI, VDD, AAI, DDI and other modes of single and multi-chamber pacing well known to the art. Circuitry 200 also preferably controls escape intervals associated with anti-tachyarrhythmia pacing in both the atrium and the ventricle, employing any anti-tachyarrhythmia pacing therapies known to the art.

Intervals defined by pacing circuitry 200 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 188, in response to stored data in memory 196 and are communicated to pacing circuitry 200 via address/data bus 190. Pacer circuitry 200 also determines the amplitude of the cardiac pacing pulses under control of microprocessor 188.

During pacing, escape interval counters within pacer timing/control circuitry 200 are reset upon sensing of R-waves and P-waves as indicated by a signals on lines 172, 176, 180 and 184 and in accordance with the selected mode of pacing on time-out trigger generation of pacing pulses by pacer output circuitry 202, 204, 206 and 208, which are coupled to electrodes 104, 106, 120, 122, 134, 136, 150 and 152. Escape interval counters are also reset on generation of pacing pulses and thereby control the basic timing of cardiac pacing functions, including anti-tachyarrhythmia pacing. The durations of the intervals defined by escape interval timers are determined by microprocessor 188 via data/address bus 190. The value of the count present in the escape interval counters when reset by sensed R-waves and P-waves may be used to measure the durations of R—R intervals, P—P intervals, P—R intervals and R—P intervals, which measurements are stored in memory 196 and used to detect the presence of tachyarrhythmias.

Microprocessor 188 most preferably operates as an interrupt-driven device, and is responsive to interrupts from pacer timing/control circuitry 200 corresponding to the occurrence of sensed P-waves and R-waves and corresponding to the generation of cardiac pacing pulses. Those interrupts are provided via data/address bus 190. Any necessary mathematical calculations to be performed by microprocessor 188 and any updating of the values or intervals controlled by pacer timing/control circuitry 200 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 188 into the pacer timing and control circuitry 200, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 188 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 188 activates cardioversion/defibrillation control circuitry 164, which initiates charging of high voltage capacitors 166 and 168 via charging circuit 210, under the control of high voltage charging control line 212. The voltage on the high voltage capacitors is monitored via VCAP line 214, which is passed through multiplexer 192 and in response to reaching a predetermined value set by microprocessor 188, results in generation of a logic signal on Cap Full (CF) line 216 to terminate charging. Thereafter, timing of the delivery of the defibrillation or cardioversion pulse is controlled by pacer timing/control circuitry 200. Following delivery of the fibrillation or tachycardia therapy microprocessor 188 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 162 under the control of control circuitry 164 via control bus 166. Output circuit 162 determines whether a monophasic or biphasic pulse is delivered, the polarity of the electrodes and which electrodes are involved in delivery of the pulse. Output circuit 162 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Although FIGS. 4 and 5 depict one electrode per cardiac chamber, the invention is not limited to a single pacing electrode per chamber. Rather, the invention may be applied to multi-chamber pacing in which there maybe two or more electrodes per chamber. For example, the invention may be applied to a bi-ventricular pacing system that includes a single electrode in the right ventricle, but three electrodes placed around the left ventricle, such as the left ventricular anterior-septum wall, the left ventricular lateral free wall, and the left ventricular posterior free wall. Multiple-site electrode placement with respect to a single cardiac chamber may, for some patients, result in more homogenous activation and homogenous mechanical response. Consequently, the invention encompasses embodiments in which a single cardiac chamber is responsive to two or more pacing stimuli.

Similarly, the invention is not limited to a single pressure sensor such as pressure sensor 114. Nor is the invention limited to a single pressure sensor per cardiac chamber. The invention encompasses any number of pressure sensors.

Figure 6:
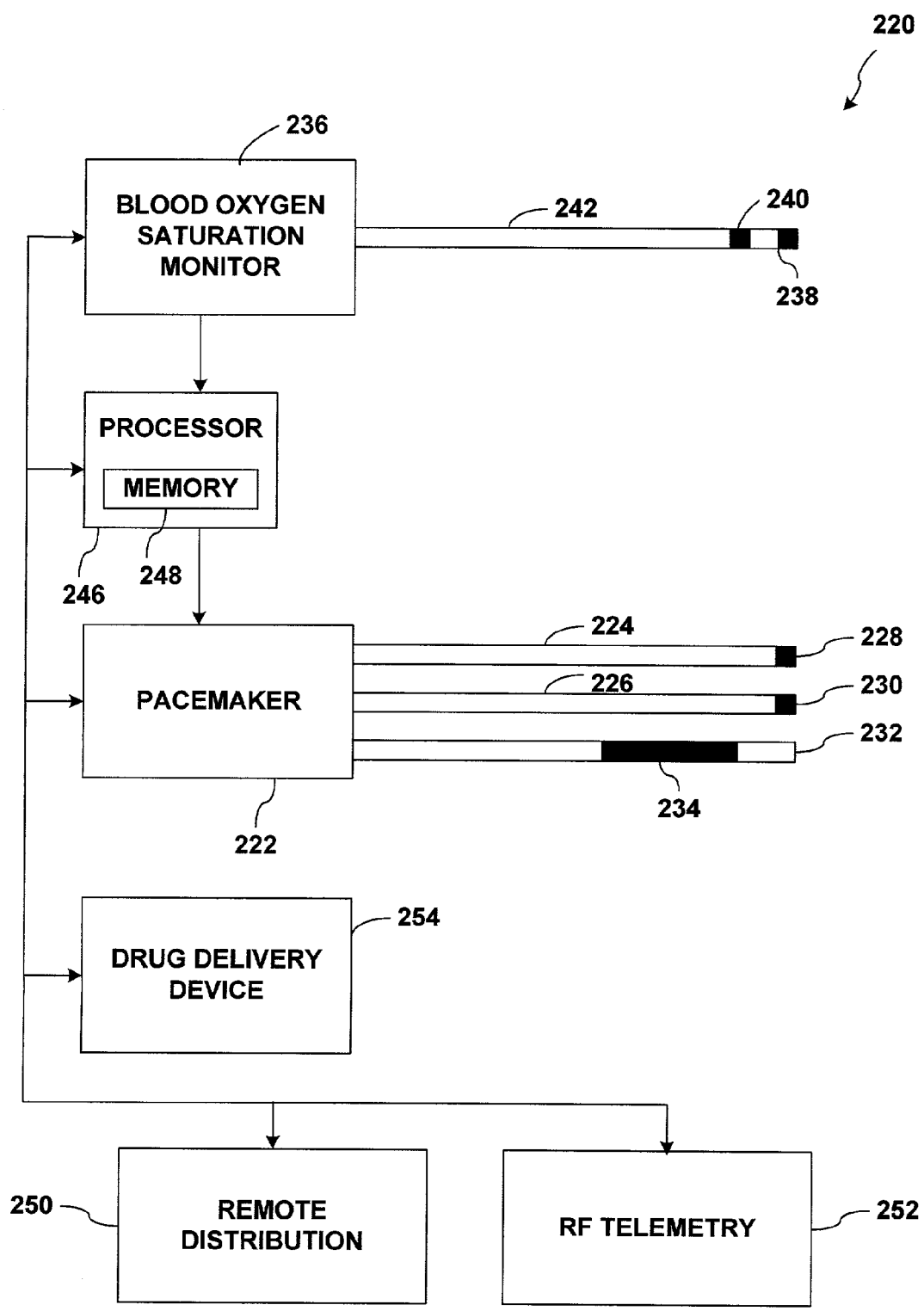
FIG. 6 is a diagram of a system including dual oxygen saturation sensors for cardiac output measurement and a cardiac pacemaker.

FIG. 6 shows a system 220 illustrating an embodiment of the invention, in which blood oxygen saturation measurements from the left and right ventricles are used to compute cardiac output using the Fick method. In some embodiments, the computed cardiac output is used to adjust the timing of pacing pulses or the interval between pacing pulses delivered by an implantable pacemaker 222 included in system 220, which may be implantable in a human being or a mammal. Pacemaker 222 includes a pulse generator that can deliver pacing pulses to two or more chambers of heart 20 (not shown in FIG. 6) using one or more pacing modes. In particular, pacemaker 222 may pace both ventricles, or may pace both atria. In the description of the embodiment that follows, it will be assumed that pacemaker 222 delivers bi-ventricular pacing. It is understood, however, that the invention may also be applied to bi-atrial pacing, or combinations of bi-atrial and/or bi-ventricular pacing. The invention may be practiced with the exemplary pacemakers shown in FIGS. 1 through 5, but the invention is not limited to the exemplary pacemakers shown in FIGS. 1 through 5.

Pacemaker 222 may be one of the many forms of implantable medical devices 10 described above, or could be an external pacemaker. Pacemaker 222 may be coupled to leads 224 and 226, which in turn are coupled to electrodes 228 and 230. Electrodes 228 and 230 may correspond to ventricular electrodes 104, 106, 150, 152 described above. Defibrillation coil electrode 234 carried by lead 232 may correspond to any of elongated coil electrodes 110, 126, 136 described above. The invention is not limited to the exemplary devices and systems shown in FIGS. 1 through 5, however. Defibrillation coil electrode 234 need not have a dedicated lead 232, but may be coupled to lead 224 or 226.

The invention includes techniques for computing cardiac output, and adjusting the timing of pacing pulses as a function of the cardiac output of a patient's heart 20. System 220 includes a blood oxygen saturation monitor 236, which is coupled to a optical sensors 238, 240 via a lead 242. Optical sensors 238, 240 can be carried by a common trans-septal lead. Alternatively, optical sensors 238, 240 may be carried by separate leads that are independently deployed in or proximate to the right and left ventricles. Moreover, optical sensors 238, 240 need not have a dedicated lead, but instead may be carried by one or both of leads 224, 226, along with sensing and stimulation eletrodes.

Optical sensors 238, 240 may be disposed in or proximate to left and right ventricles 30, 32, respectively. The invention encompasses all techniques for placement of optical sensors 238, 240. For example, optical sensors 238, 240 may be disposed on a single trans-septal lead that descends into right ventricle 32 and penetrates the interventricular septum to left ventricle 30. In this case, optical sensor 238 may be placed at the distal end of lead 242 so that optical sensor 238 is in optical communication with blood in the left ventricle. In addition, optical sensor 240 may be placed a sufficient distance away from the distal end of lead 242 so that optical sensor 240 is in optical communication with blood in the right ventricle. In another possible configuration, a separate lead carrying optical sensor 240 may descend into right ventricle 32, while a separate lead carrying optical sensor 238 may be disposed outside heart 20 and may penetrate the left ventricular wall.

Optical sensors 238, 240 are responsive to the blood oxygen saturation level inside ventricles 30, 32. Each optical sensor 238, 240 includes an emitter that emits light, e.g., infrared and red light, which is scattered and reflected by blood present in the respective ventricle 30, 32. The emitter may include two light emitting diodes, one diode for red light (e.g., at a wavelength of approximately 660 nm), and one diode for infrared light (e.g., at a wavelength of approximately 880 nm). Red light reflects color variations that are proportional to the oxygen content in oxygenated hemoglobin.

In addition, each optical sensor 238, 240 includes a receiver that receives light reflected from the blood in the ventricle 30, 32. In particular, the receiver may be sensitive to a particular wavelength of light. In an exemplary embodiment, the receiver may be an isolated, photo-sensitive diode that detects the reflected light and converts the magnitude to time intervals, which are inversely proportional to the oxygen content. Hence, the intensity of the received light is indicative of the oxygen saturation level in the blood. Reflected infrared light, independent of the oxyhemoglobin content, may be used as a reference. In particular, the interval between red and infrared light can be used as the expression of oxygen saturation. In this manner, the measurement can be made independently of variations in emission conditions affecting the reflected red and infrared light equally.

Blood oxygen saturation monitor 236 receives, monitors and analyzes the optical signals generated by optical sensors 238, 240, as will be described in more detail below. An exemplary optical saturation monitor 236 may be formed, e.g., by adapting a Chronicle™ Implantable Hemodynamic Monitor manufactured by and commercially available from Medtronic, Inc. of Minneapolis, Minn., to receive and store signals from optical sensors 238, 240. Alternatively, blood oxygen saturation monitor 236 may be realized by signal processing circuitry and programmable features of processor 246.

In one embodiment, pacemaker 222 and blood oxygen saturation monitor 236 are coupled to processor 246. Processor 246 is associated with memory 248. Memory 248 may store data such as measured parameters, identified times of cardiac chamber ejection and the results of cardiac output calculations. Processor 246 is shown as logically separate from pacemaker 222 and blood oxygen saturation monitor 236, but in practice processor 246 may be housed inside blood oxygen saturation monitor 236, or inside pacemaker 222. Processor 246 may be included in microprocessor 188 in the embodiment of implantable medical device 10 shown in FIG. 5, for example. Alternatively, processor 246 may be separate from both blood oxygen saturation monitor 236 and pacemaker 222. Further, blood oxygen saturation monitor 236, pacemaker 222 and processor 246 may be realized as a single implantable device.

Data collected by pacemaker 222, blood oxygen saturation monitor 236 and/or processor 246 may be retrieved via input/output devices such as remote distribution link 250 or RF telemetry 252. Further, pacemaker 222, blood oxygen saturation monitor 236 and/or processor 246 may receive information such as data or programming via input/output devices 250, 252. Remote distribution link 250 may provide a channel for uploading or downloading information over a telephone line or over the Internet, for example. RF telemetry 252 may communicate information on a dedicated wireless channel. Typically, a patient is required to visit an office of a physician when information is to be uploaded or downloaded via RF telemetry 252. As further shown in FIG. 6, a drug delivery device 254, implanted or external, also may be controlled by processor 246, e.g., in response to measured blood oxygen saturation data and cardiac output as described herein.

Figure 7:
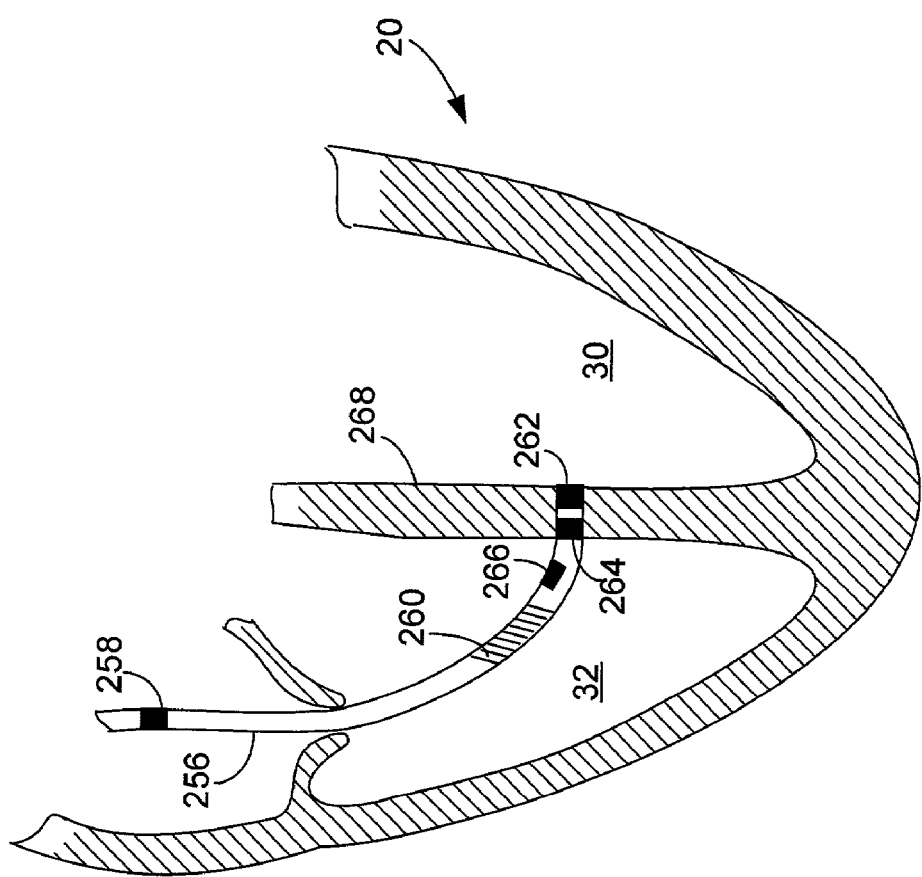
FIG. 7 is a diagram illustrating deployment of a trans-septal lead carrying dual oxygen saturation sensors.

FIG. 7 is a diagram illustrating a trans-septal lead 256 carrying dual oxygen saturation sensors within heart 20. Trans-septal lead 256 permits dual blood oxygen saturation sensors, for detecting blood oxygen saturation levels in both ventricles, to be carried by a single lead. As shown in FIG. 7, lead 256 may include an atrial electrode 258, an elongated ventricular coil electrode 260, a right ventricular blood oxygen sensor 266, and a right ventricular pacing electrode 264. A distal end 262 of lead 256 may perforate septum 268 such that the distal end is in optical communication with left ventricle 30. Electrode 264 is positioned proximate the right ventricular wall of septum 268, and is thereby positioned for pacing of right ventricle 32. An optical sensor 266 is situated a sufficient distance away from distal end 262 of lead 256 to permit optical communication with right ventricle 30. Optical sensor 266 functions as a right ventricular venous blood oxygen saturation sensor. As will be described, distal end 262 may carry a left ventricular pacing electrode and a left ventricular blood oxygen sensor.

Figure 8:
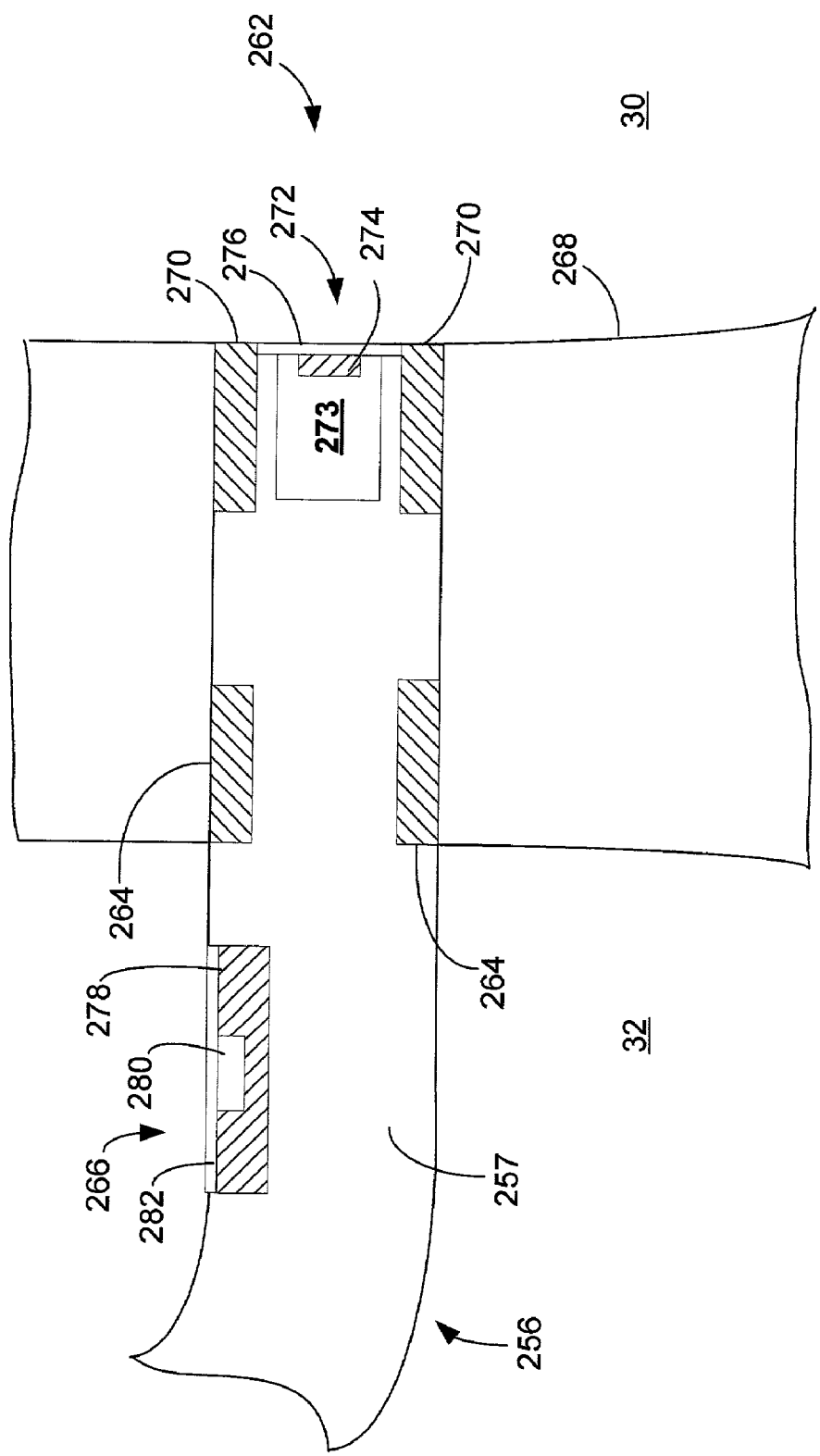
FIG. 8 is an enlarged view of the trans-septal lead of FIG. 7.
Figure 10:
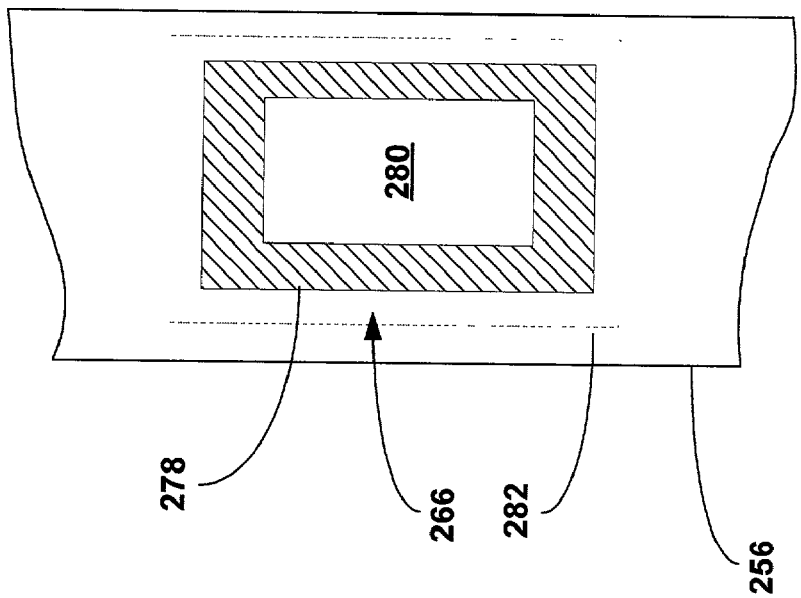
FIG. 10 is a partial side view of the trans-septal lead of FIG. 7, illustrating an oxygen saturation sensor for right ventricle measurements.
Figure 9:
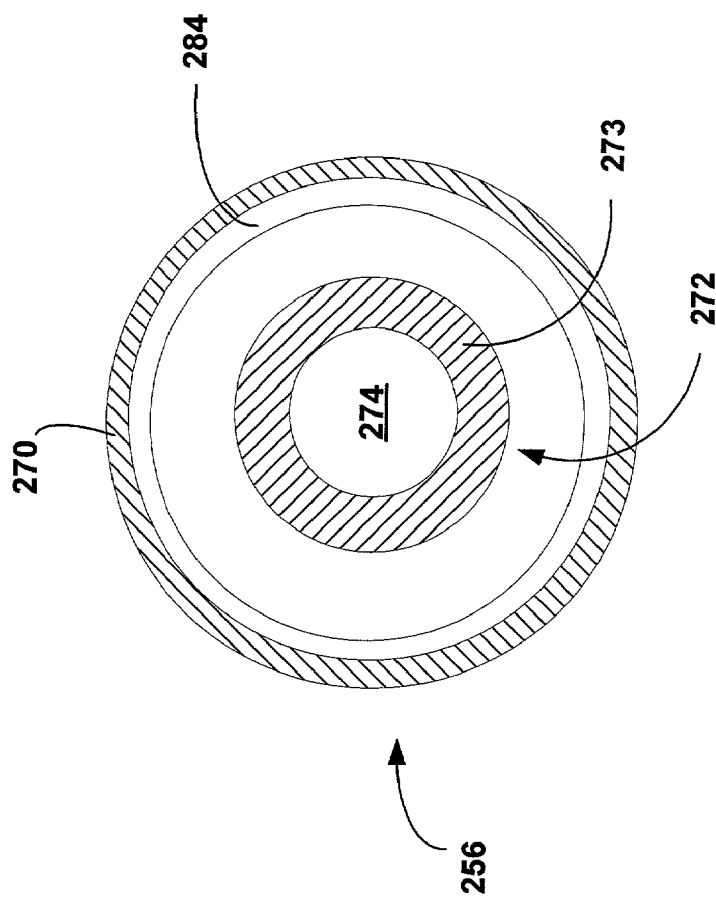
FIG. 9 is a distal end view of the trans-septal lead of FIG. 7, illustrating an oxygen saturation sensor for left ventricle measurements.

FIG. 8 is an enlarged view of trans-septal lead 256 of FIG. 7. FIG. 9 is a distal end view of trans-septal lead 256 of FIG. 7, illustrating an oxygen saturation sensor 272 for left ventricle measurements. FIG. 10 is a partial side view of the trans-septal lead 256, illustrating an oxygen saturation sensor 266 for right ventricle measurements. As shown in FIG. 8, lead 256 includes a lead body 257 having distal end 262. Lead 256 is designed for perforation and penetration of septum 268 so that distal end 262 is placed adjacent the left ventricular wall of septum 268.

Distal end 262 includes a ring-like electrode 270 that extends about lead body 257, and an optical sensor 272 that may be formed concentrically with electrode 270 and within lead body 257. Electrode 270 may be used for pacing of left ventricle 30 and, for this reason, is deployed on a side of septum 268 in substantial electrical contact with the left ventricle. A second ring-like pacing electrode 264 may be disposed on lead body 257 at a predetermined distance away from distal end 262. The predetermined distance may be selected such that, upon penetration of lead 256 within septum 268, electrode 264 is positioned adjacent the right ventricular wall of septum 268, and is therefore in substantial electrical contact with right ventricle 32.

Optical sensor 272 includes an emitter 273 and a receiver 274. Emitter 273 is oriented to emit light, e.g., infrared and red light, axially outward from distal end 262 toward arterial blood flowing within left ventricle 30. As mentioned above, emitter 273 may comprise first and second light emitting diodes. Optical sensor 272 is in substantial optical communication with the arterial blood within left ventricle 30.

Receiver 274, which may be formed concentrically with emitter 273, is oriented to receive light reflected from the blood within left ventricle 30. In particular, receiver 274 may be sensitive to reflected light indicative of oxygen content in the blood. A transmissive membrane 276 may be mounted within distal end 262 of lead 256, covering emitter 273 and receiver 274. Membrane 276 preferably is blood-compatible and selected to avoid substantial fibrous growth and thrombus formation that could obscure optical sensor 272 or cause a health risk to the patient. For example, membrane 276 may be formed from a material designed to limit thrombus formation. In a typical embodiment, membrane 276 and lead body 267 may be coated with a steroid such as dexamethasone to reduce fibrous growth and reduce inflammation.

Second optical sensor 266 is carried by lead body 257 at a predetermined distance from distal end 262. The predetermined distance may be selected such that, upon penetration of lead 256 into septum 268, second optical sensor 266 is positioned within right ventricle 32 and in optical communication with venous blood flowing in the right ventricle. Optical sensor 266 includes an emitter 278 oriented to emit light, e.g., infrared and red light, laterally outward from lead 256, and may therefore function similarly to sensor 272 as described above. In addition, optical sensor 266 includes a receiver 280 oriented to receive light reflected from venous blood flowing within right ventricle 32. A transmissive membrane 282, similar to membrane 276, may be positioned over optical sensor 266. However, this is not mandatory as venous blood is not typically thrombogenic. Optical sensors 266, 272 are illustrated conceptually in FIGS. 8 and 9 for purposes of example. For a detailed discussion of the exemplary structure of such an optical sensor, reference may be made to the description of an optical sensor for venous blood oxygen saturation measurement in "Monitoring of mixed venous oxygen saturation and pressure from biosensors in the right ventricle," A. Ohlsson et al., European Heart Journal, pages 1215–1222 (1995), the entire content of which is incorporated herein by reference.

Optical sensor 266, as well as electrodes 264, 270, and optical sensor 272, may be coupled to electrical conductors (not shown) that extend along the length of lead body 257 and interconnect with appropriate terminals in an implantable medical device, such as the implantable medical devices described above with reference to FIGS. 1–5. In particular, electrical conductors housed within lead body 257 may conduct electrical current to drive emitters 273, 278 to emit light, receive signals transduced by receivers 274, 280, and drive pacing electrodes 264, 270. Lead body 257 may include additional electrical conductors for delivery of electrical current to or from atrial electrode 258 and coil electrode 260 (FIG. 7) for sensing or pacing, as applicable. Implantation of lead 256 in septum 268 may be realized using any of a number of techniques. Lead 256 may be delivered via a guide sleeve (not shown) with a sharp edge for penetration of septum 268. Upon insertion of distal end 262 of lead 256 to a desired depth with septum 268, the guide sleeve and implantation needle can be removed. For example, when lead 256 is first threaded into heart 20, lead 256 may be surrounded by a puncture needle. The guiding sleeve can be used to guide lead 256 and the puncture needle to the desired location within heart 20. In this case, the guiding sleeve may guide lead 256 and the puncture needle to interventricular septum 268, superior to the apex of the heart.

Once the guiding catheter has guided lead 256 and the puncture needle to interventricular septum 268, the puncture needle may be used to puncture interventricular septum 268. The puncture needle may be retracted, and lead 256 can be positioned within interventricular septum 268 at a desired depth.

Figure 11:
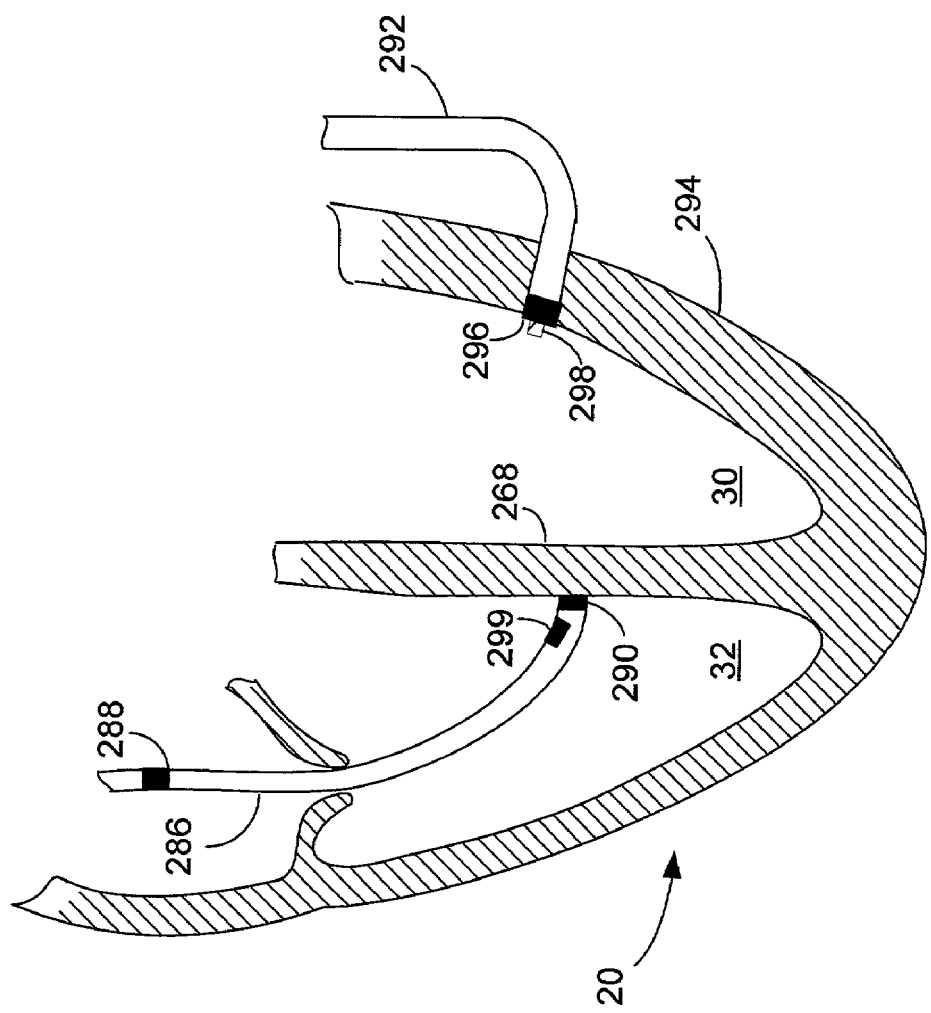
FIG. 11 is a diagram illustrating separate right and left ventricular leads for deployment of oxygen saturation sensors.

FIG. 11 is a diagram illustrating separate right and left ventricular leads 286, 292 for deployment of oxygen saturation sensors 290, 298, respectively. As an alternative to a single, trans-septal lead 256 as shown in FIGS. 8–10, FIG. 11 illustrates deployment of a first lead 292 carrying a first oxygen saturation sensor 298 for detection of the arterial blood oxygen saturation level within left ventricle 30, and a second lead 286 carrying a second oxygen saturation sensor 299 for detection of the venous blood oxygen saturation level within right ventricle 32. Lead 286 may carry additional pacing or sensing electrodes, such as atrial electrode 288 and right ventricular electrode pacing 290, as shown in FIG. 12. Similarly, lead 292 may carry a left ventricular pacing electrode 296.

Lead 286 may be positioned such that right ventricular pacing electrode 290 resides in contact with the right ventricular wall of septum 268, enabling delivery of pacing pulses to the right ventricle. In this position, optical sensor 299 is in optical communication with venous blood flowing within right ventricle 32. Lead 292 preferably penetrates epicardial wall 294 of left ventricle 30 such that left ventricular pacing electrode 296 is in electrical contact with left ventricle 30, and optical sensor 298 is in optical communication with arterial blood flowing within the left ventricle. Optical sensors 298, 299 may be substantially identical in structure and function to optical sensors 266, 272 described above with reference to FIGS. 8–10. Again, optical sensors 298, 299 detect level of light reflected from blood flowing in the ventricles to identify blood oxygen saturation levels in left and right ventricles 30, 32, respectively.

The invention permits continuous calculation of cardiac output using the blood oxygen saturation levels sensed by optical sensors in the left and right ventricles 30, 32. In particular, using Fick's method, the difference in blood oxygen saturation levels in left and right ventricles 30, 32, in combination with a hemoglobin level and an oxygen consumption level for the patient, can be used to calculate cardiac output. The hemoglobin and oxygen consumption levels can be stored in memory associated, e.g., with an implantable medical device. Advantageously, optical sensors deployed via one or more internal leads, in accordance with the invention, provide the invasive ventricular blood oxygen saturation levels required by Fick's method. The blood oxygen saturation level in the right ventricle provides a venous blood oxygen saturation level, while the blood oxygen saturation level in the left ventricle provides an arterial blood oxygen saturation level. Fick's method provides a formula for calculation of cardiac output (CO) as follows:

$$CO = \frac{\text{Oxygen Consumption (liters/minute)} \times 100}{[(\text{Arterial } O_2 \text{ } Sat) - (\text{Venous } O_2 \text{ } Sat)] \times Hb \times 0.02} \quad (1)$$

where Hb is a hemoglobin value determined for the patient. Notably, cardiac output is proportional to the difference in arterial and venous oxygen saturation. The hemoglobin value and the oxygen consumption value can be determined for a patient experimentally. Alternatively, representative values can be chosen based on patient demographics. Notably, the oxygen consumption level changes with the level of patient activity. Accordingly, the cardiac output calculation may rely on different oxygen consumption levels selected for different levels of patient activity. A useful source of demographic information relating to cardiac output and oxygen consumption versus activity level is provided in Heart and Circulation, Vol. 5, edited by C. Lentner, published by Ciba-Geigy, 1990, the entire content of which is incorporated herein by reference. Set forth below in Table 2 are data illustrating different right ventricular and left ventricular blood oxygen saturation levels, and resultant cardiac output, for a patient at rest and during 100 Watt exercise.

TABLE 2

|  | Rest | 100 W Exercise |
| --- | --- | --- |
| Venous $O_2$ Sat | 75% | 50% |
| Arterial $O_2$ Sat | 97% | 96% |
| Calculated CO | 6.1 liters/minute | 15.2 liters/minute |

The values set forth in Table 2 assume that oxygen consumption is 270 ml/minute at rest and 1400 ml/minute at 100 W exercise, and that the hemoglobin value for the patient is 10 mmol $Fe^{2+}$/liter for a male patient of 20 to 60 years of age. Typical hemoglobin ranges are described in Standard Ranges Hemoglobine, Clinical Cardiology, by Squibb, 1987, the entire content of which is incorporated herein by reference.

The calculated cardiac output can be used as a basis for adjustment of a variety of therapeutic parameters, such as pacing rate, pacing amplitude, and pacing interval, i.e., the interval between pacing pulses applied to the left and right ventricles in a BiVDD pacing device. In addition, cardiac output can be used as a basis for adjustment of the rate or amount of a therapeutic drug delivered to a patient, either internally from an implanted drug delivery device (FIG. 6) or externally from an infusion pump with intravenous delivery or other drug delivery device. Also, the calculated cardiac output may be used by a physician to set initial pacing parameters, including inter-ventricular pacing interval, for programming of an implantable medical device equipped with a pacing pulse generator to promote hemodynamic efficiency.

In some cases, it may be desirable to discriminate oxygen saturation parameters according to particular cardiac rhythms. FIG. 12 is a chart illustrating discrimination of oxygen saturation parameters for different cardiac rhythms. In operation, oxygen saturation parameters obtained over a period of time can be stored in memory and associated with different cardiac rhythms to aid a physician in analyzing the clinical status of a heart failure patient, and optimizing cardiac resynchronization therapy parameters such as inter-ventricular pacing interval, as discussed above.

Processor 246 may include a specialized module for discrimination of cardiac rhythms, such as a PR Logic™ module, manufactured by and commercially available from Medtronic Inc. of Minneapolis, Minn. Several pacing systems may include a PR Logic module, such as AT-500 pacemakers, or InSync-ICD or Gem DR implantable pacemaker-cardioverter-defibrillators, manufactured by and commercially available from Medtronic, Inc. of Minneapolis, Minn. A PR Logic module receives atrial and ventricular electrical signals, and integrates rate detection data with information about conduction patterns, regularity and AV dissociation. The PR Logic module maintains a high sensitivity for ventricular arrhythmia, and also discriminates ventricular arrhythmia from atrial arrhythmia such as supraventricular tachycardia (SVT).

As shown in FIG. 12, for example, arterial and venous oxygen saturation levels, as well as cardiac output, measured at different times can be categorized as to whether the measurements were taken during an episode of normal sinus rhythm without pacing, or during an episode of Atrio-(bi) Ventricular (A-(bi)V) pacing, or an episode of PAF (paroxysmal atrial fibrillation) with VVI pacing, or any other cardiac rhythm which can be detected and categorized by the pacemaker, which may possess P-R logic or equivalent detection algorithms. In this manner, the physician can readily discriminate between collected arterial oxygen data and venous oxygen data per cardiac rhythm group, which may be stored in separate registers in memory, if desired. The data, along with the cardiac output calculated according to the Fick method, can be graphically presented as shown in FIG. 12, e.g., on a beat-to-beat or trend basis.

Figure 13:
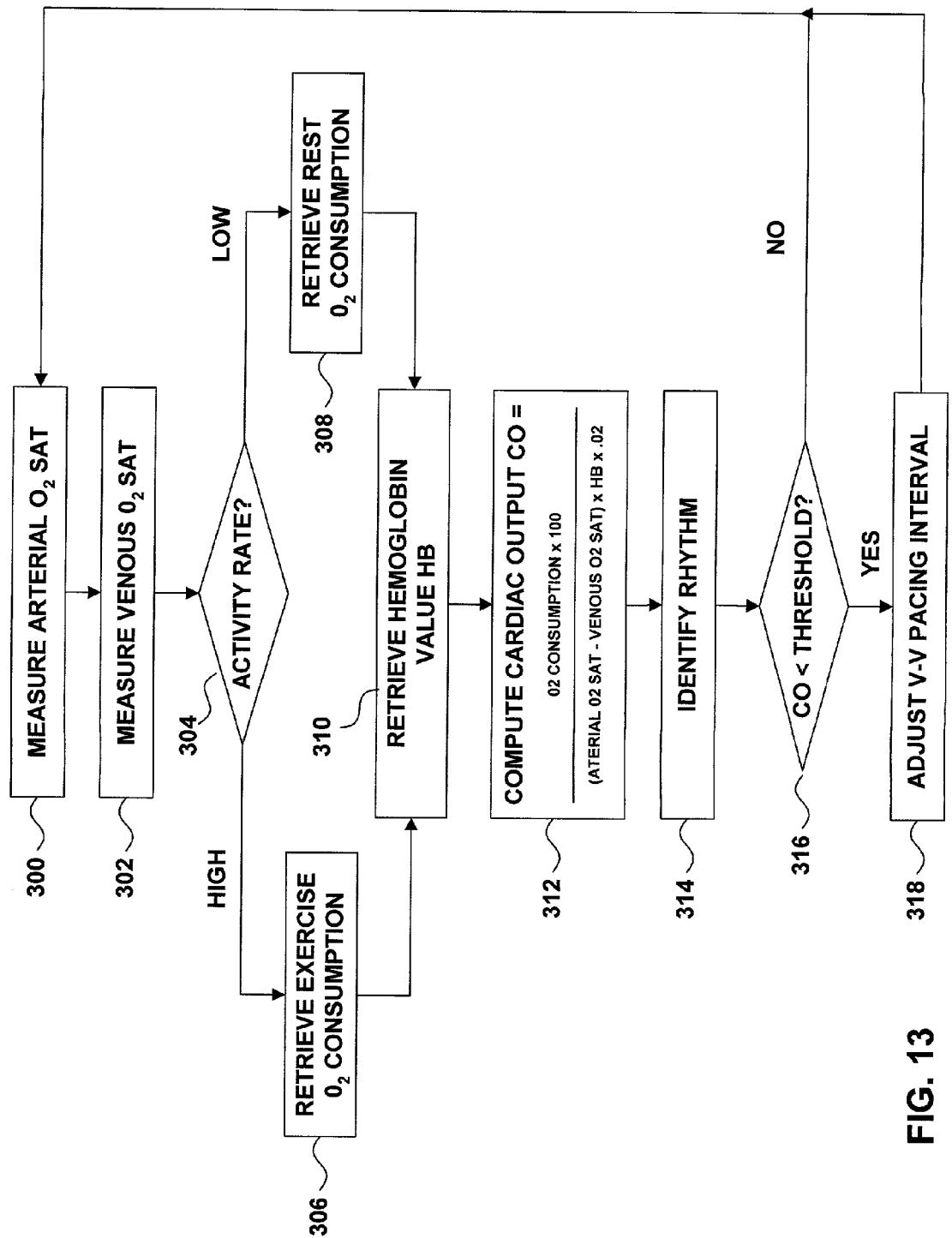
FIG. 13 is a flow diagram illustrating calculation of cardiac output for use in adjusting pacing parameters.

FIG. 13 is a flow diagram illustrating a technique for calculation of cardiac output for use in adjusting pacing parameters. As shown in FIG. 13, the technique involves measuring arterial oxygen saturation (300), measuring venous oxygen saturation (302) and determining an activity rate or level for the patient (304). The activity rate may be determined, for example, based on input from an activity level sensor. If the activity rate is high, such as during exercise, an oxygen consumption level for exercise is retrieved from memory (306). If the activity rate is low, an oxygen consumption level for rest is retrieved from memory (308). Upon retrieval of a stored hemoglobin value HB from memory (310), the cardiac output is calculated (312) according to formula (1) above.

The cardiac output measurement may be used in combination with rhythm discrimination to select a particular pacing interval for Atrio-(bi)Ventricular pacing. For example, upon identification of a particular rhythm (314), e.g., normal sinus rhythm, Atrio-(bi)Ventricular paced, or PAF with VVI pacing, the technique may involve retrieval of a particular cardiac output threshold value given the rhythm. In this case, the cardiac output is compared to an applicable threshold (316). If the cardiac output is below a given threshold, hemodynamic difficulty may be indicated. In response, the V1–V2 pacing interval may be adjusted (318) in an effort to restore hemodynamic efficiency. If the cardiac output is not below the threshold, there may be no need to adjust the pacing interval.

In either case, the process repeats for the next sensing interval, as shown in FIG. 13. For example, the oxygen saturation in the left and right ventricles, and hence the cardiac output, may be determined on a beat-by-beat basis. In this manner, when a pulse generator delivers first and second pacing pulses to the left and right ventricles during a first cardiac cycle, an oxygen saturation monitor monitors the oxygen saturation levels in the left and right ventricles during the same cardiac cycle. Then, in a subsequent cardiac cycle, the pacing interval can be adjusted as a function of the oxygen saturation levels monitored in the first cardiac cycle.

Figure 14:
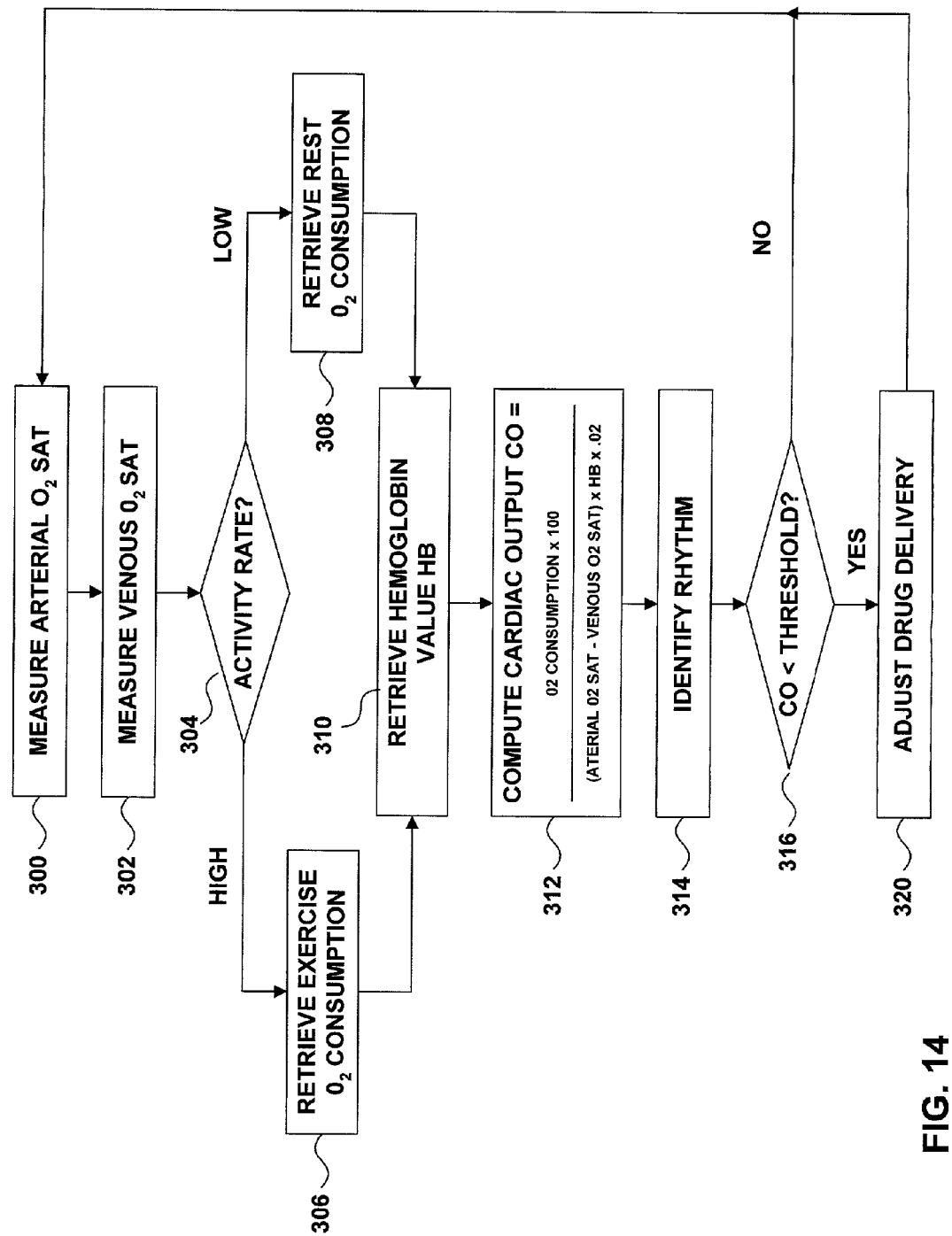
FIG. 14 is a flow diagram illustrating calculation of cardiac output for use in controlling drug delivery.

FIG. 14 is a flow diagram illustrating a technique for calculation of cardiac output for use in controlling drug delivery. The technique of FIG. 14 corresponds to the technique of FIG. 13, except that the comparison of the cardiac output to a threshold (316) is used to determine whether to adjust drug delivery (320). If the cardiac output is below the threshold, for example, indicating hemodynamic inefficiency, a drug or an increased amount of the drug may be delivered to improve hemodynamic efficiency. Also, a rate of delivery of the drug can be adjusted. In each case, the calculated cardiac output is used to adjust delivery. The techniques of FIGS. 13 and 14 may be combined such that calculated cardiac output is used to control both pacing characteristics such as V—V pacing interval and drug delivery.

The invention further includes within its scope the methods of making and using the systems described above. These methods are not limited to the specific examples described above, but may be adapted to meet the needs of a particular patient. The invention also includes within its scope any of computer-readable media comprising instructions for causing a programmable processor, such as microprocessor, to carry out the techniques described above. Such computer-readable media may include, but are not limited to read-only memory such as erasable programmable read-only memory or flash memory accessible by the processor. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. An implantable medical device comprising:
    a pulse generator that delivers a first pacing pulse to a left ventricle and a second pacing pulse to a right ventricle following a pacing interval;
    an oxygen saturation monitor that monitors a first blood oxygen saturation level in the left ventricle and a second blood oxygen saturation level in the right ventricle;
    a processor that adjusts the pacing interval as a function of the first and second blood oxygen saturation levels;
    a memory storing oxygen consumption data for the patient, wherein the processor computes cardiac output according to the Fick method based on the first and second blood oxygen saturation levels and the oxygen consumption data, and the hemoglobin data, and adjusts the pacing interval as a function of the computed cardiac output; and
    an activity level sensor that senses an activity level of the patient, wherein the memory stores oxygen consumption data for different activity levels of the patient, and the processor computes the cardiac output based on oxygen consumption data in the memory that corresponds to the sensed activity level.

2. An implantable medical device comprising:
    a pulse generator that delivers a first pacing pulse to a left ventricle and a second pacing pulse to a right ventricle following a pacing interval;
    an oxygen saturation monitor that monitors a first blood oxygen saturation level in the left ventricle and a second blood oxygen saturation level in the right ventricle; and
    a processor that adjusts the pacing interval as a function of the first and second blood oxygen saturation levels;
    a memory storing oxygen consumption data for the patient, wherein the processor computes cardiac output according to the Fick method based on the first and second blood oxygen saturation levels and the oxygen consumption data, and the hemoglobin data, and adjusts the pacing interval as a function of the computed cardiac output
    wherein the oxygen saturation monitor includes:
        a first optical sensor carried on a lead for deployment in the left ventricle of a patient to measure the blood oxygen saturation level in the left ventricle; and
        a second optical sensor carried on a lead for deployment in the right ventricle of the patient to measure the blood oxygen saturation level in the right ventricle.

3. An implantable medical device comprising:
    a pulse generator that delivers a first pacing pulse to a left ventricle and a second pacing pulse to a right ventricle following a pacing interval;
    an oxygen saturation monitor that monitors a first blood oxygen saturation level in the left ventricle and a second blood oxygen saturation level in the right ventricle; and
    a processor that adjusts the pacing interval as a function of the first and second blood oxygen saturation levels; and
    a memory storing oxygen consumption data for the patient, wherein the processor computes cardiac output according to the Fick method based on the first and second blood oxygen saturation levels and the oxygen consumption data, and the hemoglobin data, and adjusts the pacing interval as a function of the computed cardiac output,
    wherein the oxygen saturation monitor comprises a first optical sensor and a second optical sensor which are carried on a common lead, lead including a lead body having a distal tip, and wherein:
        the first optical sensor is carried by the lead body adjacent the distal tip, wherein the first optical sensor includes a first emitter oriented to emit light outward from the distal tip and a first receiver oriented to receive light reflected toward the distal tip, and
        the second optical sensor includes a second emitter oriented to emit light laterally outward from a side of the lead body and a second receiver oriented to receive light reflected toward the side of the lead body.

4. The implantable medical device of claim 3, wherein the lead body includes a transmissive membrane that permits emission and reception of light by the first and second optical sensors.

5. The implantable medical device of claim 3, wherein each of the first and second emitters includes a first light emitting diode that emits infrared light and a second light emitting diode that emits red light.

6. The implantable medical device of claim 3, wherein the second optical sensor is carried by the lead body at a distance from the distal tip, wherein the distance is selected such that the second optical sensor is exposed to the right ventricle of a heart upon positioning of the lead body through the septum to place the first optical sensor within the left ventricle.

7. The implantable medical device of claim 3, further comprising at least one electrode formed on the lead body.

8. The implantable medical device of claim 3, further comprising:
    a first electrode carried adjacent the distal tip of the lead body; and
    a second electrode carried by the lead body at a distance from the distal tip, wherein the distance is selected such that second electrode is in substantial conductive contact with the right ventricle of a heart upon positioning of the lead body through the septum to place the first electrode in substantial conductive contact with the left ventricle.

9. The implantable medical device of claim 3, further comprising first and second electrodes carried by the lead body between the distal tip and the second optical sensor.

10. The implantable medical device of claim 3, wherein the processor computes the cardiac output further based on a hemoglobin value determined for the patient.

11. A method comprising:
delivering a first pacing pulse to a left ventricle of a patient;
delivering a second pacing pulse to a right ventricle following a pacing interval;
monitoring a first blood oxygen saturation level in the left ventricle and a second blood oxygen saturation level in the right ventricle; and
adjusting the pacing interval as a function of the first and second blood oxygen saturation levels
computing cardiac output according to the Fick method based on the first and second blood oxygen saturation levels and oxygen consumption data determined for the patient, wherein adjusting the pacing interval includes adjusting the pacing interval as a function of the computed cardiac output;
sensing an activity level of the patient, and computing the cardiac output based on oxygen consumption data that corresponds to the sensed activity level.

12. A method comprising:
delivering a first pacing pulse to a left ventricle of a patient;
delivering a second pacing pulse to a right ventricle following a pacing interval;
monitoring a first blood oxygen saturation level in the left ventricle and a second blood oxygen saturation level in the right ventricle; and
adjusting the pacing interval as a function of the first and second blood oxygen saturation levels; and
sensing the blood oxygen saturation levels using:
a first optical sensor carried on a lead deployed in the left ventricle of a patient to measure the blood oxygen saturation level in the left ventricle; and
a second optical sensor carried on a lead deployed in the right ventricle of the patient to measure the blood oxygen saturation level in the right ventricle.

13. The method of claim 12, wherein the first and second optical sensors are carried on a common lead, the lead includes a lead body having a distal tip, and wherein:
the first optical sensor is carried by the lead body adjacent the distal tip, wherein the first optical sensor includes a first emitter oriented to emit light outward from the distal tip and a first receiver oriented to receive light reflected toward the distal tip, and
the second optical sensor includes a second emitter oriented to emit light laterally outward from a side of the lead body and a second receiver oriented to receive light reflected toward the side of the lead body.

14. The method of claim 13, wherein the lead body includes a transmissive membrane that permits emission and reception of light by the first and second optical sensors.

15. The method of claim 13, wherein each of the first and second emitters includes a first light emitting diode that emits infrared light and a second light emitting diode that emits red light.

16. The method of claim 13, wherein the second optical sensor is carried by the lead body at a distance from the distal tip, wherein the distance is selected such that the second optical sensor is exposed to the right ventricle of a heart upon positioning of the lead body through the septum to place the first optical sensor within the left ventricle.

17. The method of claim 13, further comprising at least one electrode formed on the lead body.

18. The method of claim 13, wherein the lead includes:
a first electrode carried adjacent the distal tip of the lead body; and
a second electrode carried by the lead body at a distance from the distal tip, wherein the distance is selected such that second electrode is in substantial conductive contact with the right ventricle of a heart upon positioning of the lead body through the septum to place the first electrode in substantial conductive contact with the left ventricle.

19. The method of claim 13, wherein the lead includes first and second electrodes carried by the lead body between the distal tip and the second optical sensor.

20. The method of claim 13, further comprising computing cardiac output based on a hemoglobin value determined for the patient.

21. A computer-readable medium comprising instructions that cause a processor to:
control a pulse generator to deliver a first pacing pulse to a left ventricle of a patient, and deliver a second pacing pulse to a right ventricle following a pacing interval;
monitor a first blood oxygen saturation level in the left ventricle and a second blood oxygen saturation level in the right ventricle; and
adjust the pacing interval as a function of the first and second blood oxygen saturation levels
wherein the instruction cause a processor to sense an activity level of the patient, and compute the cardiac output based on oxygen consumption data that corresponds to the sensed activity level.

22. A computer-readable medium comprising instructions that cause a processor to:
control a pulse generator to deliver a first pacing pulse to a left ventricle of a patient, and deliver a second pacing pulse to a right ventricle following a pacing interval;
monitor a first blood oxygen saturation level in the left ventricle and a second blood oxygen saturation level in the right ventricle; and
adjust the pacing interval as a function of the first and second blood oxygen saturation levels
wherein the instructions cause the processor to compute the cardiac output based on a hemoglobin value determined for the patient.

23. An implantable medical device comprising:
means for delivering a first pacing pulse to a left ventricle of a patient;
means for delivering a second pacing pulse to a right ventricle following a pacing interval;
means for monitoring a first blood oxygen saturation level in the left ventricle and a second blood oxygen saturation level in the right ventricle; and
means for adjusting the pacing interval as a function of the first and second blood oxygen saturation levels;
means for computing cardiac output according to the Fick method based on the first and second blood oxygen saturation levels and oxygen consumption data determined for the patient, wherein the means for adjusting the pacing interval includes means for adjusting the pacing interval as a function of the computed cardiac output; and means for sensing an activity level of the patient, wherein the means for computing computes the cardiac output based on oxygen consumption data that corresponds to the sensed activity level.

24. An implantable medical device comprising:
means for delivering a first pacing pulse to a left ventricle of a patient;
means for delivering a second pacing pulse to a right ventricle following a pacing interval;
means for monitoring a first blood oxygen saturation level in the left ventricle and a second blood oxygen saturation level in the right ventricle; and
means for adjusting the pacing interval as a function of the first and second blood oxygen saturation levels; and
means for computing cardiac output according to the Fick method based on the first and second blood oxygen saturation levels and oxygen consumption data determined for the patient, wherein the means for adjusting the pacing interval includes means for adjusting the pacing interval as a function of the computed cardiac output,
wherein the means for monitoring the blood oxygen saturation levels includes:
a first optical sensor carried on a lead deployed in the left ventricle of a patient to measure the blood oxygen saturation level in the left ventricle; and
a second optical sensor carried on a lead deployed in the right ventricle of the patient to measure the blood oxygen saturation level in the right ventricle.

25. The implantable medical device of claim 24, wherein the first and second optical sensors are carried on a common lead, the lead includes a lead body having a distal tip, and wherein:
the first optical sensor is carried by the lead body adjacent the distal tip, wherein the first optical sensor includes a first emitter oriented to emit light outward from the distal tip and a first receiver oriented to receive light reflected toward the distal tip, and
the second optical sensor includes a second emitter oriented to emit light laterally outward from a side of the lead body and a second receiver oriented to receive light reflected toward the side of the lead body.

26. The implantable medical device of claim 25, wherein the lead body includes a transmissive membrane that permits emission and reception of light by the first and second optical sensors.

27. The implantable medical device of claim 25, wherein each of the first and second emitters includes a first light emitting diode that emits infrared light and a second light emitting diode that emits red light.

28. The implantable medical device of claim 25, wherein the second optical sensor is carried by the lead body at a distance from the distal tip, wherein the distance is selected such that the second optical sensor is exposed to the right ventricle of a heart upon positioning of the lead body through the septum to place the first optical sensor within the left ventricle.

29. The implantable medical device of claim 25, further comprising at least one electrode formed on the lead body.

30. The implantable medical device of claim 25, wherein the lead includes:
a first electrode carried adjacent the distal tip of the lead body; and
a second electrode carried by the lead body at a distance from the distal tip, wherein the distance is selected such that second electrode is in substantial conductive contact with the right ventricle of a heart upon positioning of the lead body through the septum to place the first electrode in substantial conductive contact with the left ventricle.

31. The implantable medical device of claim 25, wherein the lead includes first and second electrodes carried by the lead body between the distal tip and the second optical sensor.

32. The implantable medical device of claim 25, wherein the means for computing includes means for computing cardiac output based on a hemoglobin value determined for the patient.

* * * * *